(12) United States Patent
Diaz et al.

(10) Patent No.: US 11,325,974 B2
(45) Date of Patent: *May 10, 2022

(54) CHECKPOINT BLOCKADE AND MICROSATELLITE INSTABILITY

(71) Applicant: The Johns Hopkins University, Baltimore, MD (US)

(72) Inventors: Luis Diaz, Ellicot City, MD (US); Bert Vogelstein, Baltimore, MD (US); Kenneth W. Kinzler, Baltimore, MD (US); Nickolas Papadopoulos, Towson, MD (US); Dung Le, Lutherville, MD (US); Drew M. Pardoll, Brookville, MD (US); Suzanne L. Topalian, Brookville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/131,326

(22) Filed: Dec. 22, 2020

(65) Prior Publication Data
US 2021/0130463 A1 May 6, 2021

Related U.S. Application Data

(63) Continuation of application No. 16/144,549, filed on Sep. 27, 2018, now Pat. No. 10,934,356, which is a continuation of application No. 15/523,451, filed as application No. PCT/US2015/060331 on Nov. 12, 2015.

(60) Provisional application No. 62/190,977, filed on Jul. 10, 2015, provisional application No. 62/079,357, filed on Nov. 13, 2014.

(51) Int. Cl.
| | |
|---|---|
| *G01N 31/00* | (2006.01) |
| *G01N 33/53* | (2006.01) |
| *C07K 16/28* | (2006.01) |
| *C12Q 1/6886* | (2018.01) |
| *C07K 16/30* | (2006.01) |
| *C07K 16/40* | (2006.01) |
| *A61K 39/00* | (2006.01) |

(52) U.S. Cl.
CPC ...... *C07K 16/2803* (2013.01); *C07K 16/2818* (2013.01); *C07K 16/2827* (2013.01); *C07K 16/30* (2013.01); *C07K 16/40* (2013.01); *C12Q 1/6886* (2013.01); *C12Y 113/11052* (2013.01); *A61K 2039/505* (2013.01); *A61K 2039/55* (2013.01); *C07K 2317/00* (2013.01); *C07K 2317/24* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 10,934,356 B2 * | 3/2021 | Diaz | ............ C07K 16/40 |
| 2010/0055102 A1 | 3/2010 | Langermann | |
| 2013/0309250 A1 | 11/2013 | Cogswell et al. | |
| 2015/0210769 A1 | 7/2015 | Freeman | |
| 2017/0175197 A1 | 6/2017 | Gatalica | |
| 2019/0023787 A1 | 1/2019 | Diaz | |

FOREIGN PATENT DOCUMENTS

| | | |
|---|---|---|
| CA | 2935432 | 7/2015 |
| CN | 102230004 | 11/2011 |
| CN | 102414565 | 4/2012 |
| JP | 2005/518798 | 6/2005 |
| WO | WO 2003/072822 | 9/2003 |
| WO | WO 2004/056875 | 7/2004 |
| WO | WO 20054)64009 | 7/2005 |
| WO | WO 2006/121168 | 11/2006 |
| WO | WO 2008/083174 | 7/2008 |
| WO | WO 2009/101611 | 8/2009 |
| WO | WO 2009/114335 | 9/2009 |
| WO | WO 2010/036959 | 4/2010 |
| WO | WO 2013/190555 | 12/2013 |
| WO | WO 2015/112900 | 7/2015 |
| WO | WO 2016/077553 | 5/2016 |

OTHER PUBLICATIONS

Lipson et al. (Clin Cancer Res. vol. 19, No. 2, pp. 462-468, 2013). (Year: 2013).*
Lipson et al. (Clinical Cancer Research, 2013, 19(2), pp. 462-468, published online Nov. 20, 2012) (Year: 2012).*
Llosa et al. Journal of Clinical Oncology, 2014, vol. 32, No. 15_Suppl., pp. 3620-3620, published online May 20, 2014) (Year: 2014).*
Durie et al. Journal of Clinical Oncology, 2011, vol. 29, No. 4_Suppl,pp. 392, published online Feb. 1, 2011). (Year: 2011).*
Zeynep Eroglu (Personalized medicine in Oncology, Apr. 2014, Part l). (Year: 2014).*
Dung et al. (Journal of Clinical Oncology, 2014, vol. 32, No. 15, Suppl. Published online May 20, 2104). (Year: 2014).*
Lau, Ester. The Lancet, Oncology, Epub. Jun. 7, 2015, vol. 16, No. 7, e319. (Year: 2015).*
Acopost.com [online], "on PD-1 Blockade in Tumors With Mismatch Repair Deficiency with Dung T. Le, MD and Axel Grothey, MD," 2015, [retrieved on Feb. 4, 2020], retrieved from URL<https://www.ascopost.com/archive/meetings/2015-asco-annual-meeting/dung-t-le-md-and-axel-grothey-md-on-pd-1-blockade-in-tumors-with-mismatch-repair-deficiency/> 4 pages.

(Continued)

*Primary Examiner* — Lisa V Cook
(74) *Attorney, Agent, or Firm* — Fish & Richardson P.C.

(57) ABSTRACT

Blockade of immune checkpoints such as cytotoxic T-lymphocyte antigen-4 (CTLA-4) and programmed death-1 (PD-1) shows promise in patients with cancer. Inhibitory antibodies directed at these receptors have been shown to break immune tolerance and promote anti-tumor immunity. These agents work particularly well in patients with a certain category of tumor. Such tumors may be particularly susceptible to treatment because of the multitude of neoantigens which they produce.

7 Claims, 13 Drawing Sheets

(56) References Cited

OTHER PUBLICATIONS

Agaram NP, Shia J, Tang LH, Klimstra DS. DNA mismatch repair deficiency in ampullary carcinoma: a morphologic and immunohistochemical study of 54 cases. American journal of clinical pathology 2010;133:772-80.

Alexander J, Watanabe T, Wu TT, Rashid A, Li S, Hamilton SR. Histopathological identification of colon cancer with micro satellite instability. The American journal of pathology 2001;158:527-35.

Ansell SM, Lesokhin AM, Borrello I, et al. PD-1 Blockade with Nivolumab in Relapsed or Refractory Hodgkin's Lymphoma. The New England journal of medicine 2015;372:311-9.

Bacher (Disease Markers, vol. 20, p. 237-250, 2004) (Year: 2004).

Bass et al., Comprehensive molecular characterization of gastric adenocarcinoma. Nature 2014;513:202-9.

Beltran et al., "Targeted Next-generation Sequencing of Advanced Prostate Cancer Identifies Potential Therapeutic Targets and Disease Heterogeneity," European Urology, May 2013, 63(5):920-926.

Berger MF, Hodis E, Heffernan TP, et al. Melanoma genome sequencing reveals frequent PREX2 mutations. Nature 2012;485:502-6.

Bodmer W, Bishop T, Kanan P. Genetic steps in colorectal cancer. Nature genetics 1994:6:217-9.

Boland CR, Goel A. Microsatellite instability in colorectal cancer. Gastroenterology 2010;138:2073-87 e3.

Brahmer JR, Drake CG, Wollner I, et al. Phase I study of single-agent antiprogrammed death-1 (MDX-1106) in refractory solid tumors: safety, clinical activity, pharmacodynamics, and immunologic c01Telates. Journal of clinical oncology: official journal of the American Society of Clinical Oncology 2010;28:3167-75.

Brahmer JR, Tykodi SS, Chow LQ, et al. Safety and activity of anti-PD-L1 antibody in patients with advanced cancer. The New England journal of medicine 2012:366:2455-65.

Bristol-Myers Squibb (Clinical Trial Announcement NCT02060188, published Feb. 11, 2014) (Year: 2014).

Canadian Office Action in Application No. 2966660, dated Mar. 22, 2019.

Champiats et al., "Exomics and immunogenics: Bridging Mutational load and immune checkpoints efficacy", Oncoimmunology, Jan. 16, 2014, vol. 3, No. 1 pp. e27817.

Chen L., "Co-inhibitory molecules of the B7-CD28 family in the control of T cell immunity", Nat. Rev. Immunol 2004: 4: 336-47.

Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer". Oct. 30, 2014.

Comprehensive molecular characterization of human colon and rectal cancer. Nature 2012;487:330-7.

D'Andrea et al., "The Fanconi Anaemia/BRCA Pathway," Nature Reviews, Jan. 2003, 3:23-34.

Davis J. L. et al., "Loss of Heterozygosity and Microsatellite Instability are rare in Sporadic Dedifferentiated Liposarcoma", Arch Pathol Lab Med., Jun. 2014, vol. 138, pp. 823-827.

Diaz LA, Jr., Bardelli A. Liquid biopsies: genotyping circulating tumor DNA.Jumal of clinical oncology : official journal of the American Society of Clinical Oncology 2014;32:579-86.

Disis M.L., "Mechanism of action of immunotherapy", Semin Oncol, Sep. 6, 2014, vol. 41, No. Suppl 5, pp. S3-S12 Table 2.

Dolcetti (American Journal of Pathology, vol. 154, p. 1805-1813, 1999) (Year: 1999).

Dolcetti R, Viel A, Doglioni C, et al. High prevalence of activated intraepithelial cytotoxic T lymphocytes and increased neoplastic cell apoptosis in colorectal carcinomas with microsatellite instability. The American journal of pathology 1999;154:1805-13.

Dong et al., "Tumor-associated B7-H1 promotes T-cell apoptosis: A potential mechanism of immune evasion," Nature Medicine, 2002, 8(8):793-800.

"Drugs.com" [online] "FDA Approves Keytruda (pembrolizumab) as First Cancer Treatment for any Solid Tumor with a specific Genetic Feature", May 23, 2017 [retrieved on Jul. 19, 2018], Retrieved from the Internet: URL<https://www.drugs.com/newdrugs/fda-approves-keytruda-pembrolizumab-firs-cancer-any-solid-tumor-specific-genetic-feature-4538.html, 3 pages.

"Drugs.com" [online] "FDA Approves Keytruda", Sep. 4, 2014 [retrieved on May 29, 2018] Retrieved from the Internet: URL https://www.drugs.com/newdrugs/fda-approves-keytruda-pembrolizumab-advanced-melanoma-4079.html.

"Drugs.com" [online] "FDA Approves Opdivo", Dec. 22, 2014 [retrieved on May 29, 2018] Retrieved from the Internet: URL https://www.drugs.com/newdrugs/fda-approves-opdivo-nivolumab-advanced-melanoma-4133.html.

"Drugs.com" [online] "FDA Expands Approved use of Opdivo (nivolumab) to Treat Lung Cancer", Mar. 4, 2015 [retrieved on May 29, 2018] Retrieved from the Internet: URL https://www.drugs.com/newdrugs/fda-expands-approved-opdivo-nivolumab-lung-cancer-4179.html.

Eshleman et al., "Increased mutation rate at the hprt locus accompanies microsatellite instability in colon cancer", Oncogene 1995; 10: 33-7.

European Search Report in Application No. 15858277.5, dated May 14, 2018, 8 pages.

Galon (Science, vol. 313, p. 1960-1964, 2006) (Year: 2006).

Garg K. et al., "Selection of endometrial carcinomas for DNA mismatch repair protein immunohistochemistry using patient age and tumor morphology enhances detection of mismatch repair abnormalities", The American journal of surgical pathology 2009;33:925-33.

Gatalica Z. et al., "Programmed death 1 (PD-1) lymphocytes and ligand (PD-1) in colorectal cancer and their relationship to microsatellite instability status", J. Clin. Oncol., May 2014, vol. 32, No. 15, Suppl. 1, Abstract No. 3625.

Goldstein J, Tran B, Ensor J, et al. Multicenter retrospective analysis of metastatic colorectal cancer (CRC) with high-level microsatellite instability (MSI-H). Annals of oncology : official journal of the European Society for Medical Oncology/ESMO 2014;25:1032-8.

Grasso et al., "The mutational landscape of lethal castration-resistant prostate cancer," Nature, May 2012, 487:239-243.

Greenman et al., "Patterns of somatic mutation in human cancer genomes," Nature, 446:153-158, 2007.

Gubin MM, Zhang X, Schuster H, et al. Checkpoint blockade cancer immunotherapy targets tumour-specific mutant antigens. Nature 2014:515:577-81.

Hamid 0, Robert C, Daud A, et al. Safety and tumor responses with lambrolizumab ( anti-PD-1) I melanoma. The New England journal of medicine 2013;369:134-44.

Hay et al., "Clinical development success rates for investigational drugs", Nature Biotechnology, vol. 32, No. 1, pp. 40-51, 2014.

Herbst RS, Soria JC, Kowanetz M, et al. Predictive correlates of response to the anti-PD-L1 antibody MPDL3280A in cancer patients. Nature 2014;515:563-7.

Herman JG, Umar A, Polyak K, et al. Incidence and functional consequences of hMLHl promoter hypermethylation in colorectal carcinoma. Proceedings of the National Academy of Sciences of the United States of America 1998;95:6870-5.

Internation Search Report in International Application No. PCT/US2015/012754, dated Apr. 24, 2015.

International Preliminary Report on Patentability in International Application No. PCT/US2015/060331, dated May 16, 2017, 9 pages.

International Search Report for PCT/US2015/060331, dated Feb. 24, 2016.

Japanese Office Action in Japanese Patent Application No. 2017-525894, dated Feb. 16, 2018.

Ji (Cancer Immunology Immunotherapy, vol. 61, p. 1019-1031, 2012) (Year: 2012).

Jones S, Anagnostou V, Lytle K, et al. Personalized genomic analyses for cancer mutation discovery and interpretation. Science translational medicine 2015;7:283ra53.

Jones S, Emmerson P, Maynard J, et al. Biallelic germline mutations in MYH predispose to multiple colorectal adenoma and somatic G:C—T:A mutations. Human Molecular Genetics 2002; 11:2961-7.

(56) References Cited

OTHER PUBLICATIONS

Kandoth C, Schultz N, Cherniack AD, et al. Integrated genomic characterization of endometrial carcinoma. Nature 2013;497:67-73.
Kanopiene et al., "Endometrial cancer and microsatellite instability status," Open Medicine, 2015, 10(1):70-76.
KEYTRUDA® Label (Nov. 2017).
KEYTRUDA® Label (Nov. 2018).
Kim H, Jen J, Vogelstein B, Hamilton SR. Clinical and pathological characteristics of sporadic colorectal carcinomas with DNA replication errors in microsatellite sequences. The American journal of pathology 1994:145:148-56.
Kirkwood et al., "Immunotherapy of cancer in 2012", CA: A Cancer Journal for Clinicians, vol. 62, No. 5, Sep. 1, 2012, pp. 309-335.
Kolata et al., "Cancer Drug Proves to Be Effective Against Multiple Tumors," The New York Times, 2017, 4 pages.
Koopman M, Kollman GAM, Mekenkamp L, et al. Deficient mismatch repair system in patients with sporadic advanced colorectal cancer. Br J Cancer 2000;100:266-73.
Lacombe et al., "The dream and reality of histology agnostic cancer clinical trials," Molecular Oncology, Sep. 2014, 8(6):1057-1063.
Lau et al., "Mismatch repair deficiency predicts benefit of anti-PD-1 therapy", The Lancet Oncology, Epub. Jun. 7, 2015, vol. 16, No. 7, e319.
Le et al., "Phase 2 Study of programmed death-1 antibody (anti-PD-1, MK-3475) in patients with microsatellite unstable (MSI) tumors", J. Clin. Oncol, May 2014, vol. 32, No. 15, Suppl. 1, Abstract No. TPS3128.
Le et al., "Mismatch repair deficiency predicts response of solid tumors to PD-1 blockade," Science, 2017, 357(6349):409-413.
Le et al., "PD-1 Blockade in Tumors with Mismatch-Repair Deficiency," The New England Journal of Medicine, 2015, 372(26):2509-2520.
Le et al., Phase 2 Study of programmed death-1 antibody (antu-PD-1, MK-3475) inpatients with microsatellite unstable (MSI) tumors. Jun. 1, 2014.
Lee et al., "Novel Therapies in Development for Metastatic Colorectal Cancer," S2-S7 Sep. 30, 2014 vol. 7, No. 4.
Lee et al., "Novel Therapies in Development for Metatatic Colorectal Cancer," Gastrointestinal Cancer Research, 2014, 7(4 Suppl 1):S2-S7.
Lee et al., "The mutation spectrum revealed by paired genome sequences from a lung cancer patient," Nature, 2010, 465:473-477.
Linnemann C. et al., High-throughput epitope discovery reveals frequent recognition of neo-antigens by CD4+ T cells in human melanoma, Nature medicine 2015; 21: 81-5.
Liosa, N.J. et al., "Immune checkpoints expression in MSI versus MSS colorectal cancers and their potential therapeutic implications", J. Clin. Oncol., May 2014, vol. 32, No. 15, Suppl. 1, Abstract No. 3620.
Lipson EJ, Velculescu VE, Pritchard TS, et al. Circulating tumor DNA analysis as a real-time method for monitoring tumor burden in melanoma patients undergoing treatment with immune checkpoint blockade. Journal for immunotherapy of cancer 2014;2:42.
Lipson et al., "Durable cancer regression off treatment and effective reinduction therapy with an anti-PD-1 antibody," Clinical cancer research, an official journal of the American Association for Cancer Research, 2013;19:462-468.
Lipson et al., "PD-L1 Expression in the Merkel Cell Carcinoma Microenvironment: Association with Inflammation, Merkel Cell Polyomavirus, and Overall Survival", Cancer Immunol Res. 1(1), 54-63, 2013.
Llosa et al., "Immune chckpoints expression in MSI versus MSS colorectal cancers and their potential therapeutic implications", Journal of Clinical Oncology, vol. 32, No. 15, May 20, 2014.
Llosa, Nicolas J., et al., 'The vigorous immune microenvironment of microsatellite instable colon cancer is balanced by multiple counter-inhibitory checkpoints', Cancer Discovery, Epub. Oct. 30, 2014, vol. 6, No. 1, pp. 43-51 (NIH Public Access Author Manuscript Version internal pp. 1-18).

Lundegaard C, Lamberth K, Hamdahl M, Buus S, Lund 0, Nielsen M. NetMHC-3.0: accurate web accessible predictions of human, mouse and monkey MHC class I affinities for peptides of length 8-11. Nucleic acids research 2008;36:W509-12.
Lundegaard C, Lund 0, Nielsen M. Accurate approximation method for prediction of class I MHC affinities for peptides of length 8, 10 and 11 using prediction tools trained on 9mers. Bioinformatics 2008;24:1397-8.
Lynch HT, de la Chapelle A. "Hereditary colorectal cancer", The New England journal of medicine 2003;348:919-32.
Macherla et al., "Emerging Role of Immune Checkpoint Blockade in Pancreatic Cancer," Int J Mol Sci. Nov. 2018; 19(11): 3505.
Maple et al., "Defective DNA mismatch repair in long-term (> or =3 years) survivors with pancreatic cancer", Pancreatology 2005; 5: 220-7; discussion 7-8.
McGinley et al., "This is not the end': Using immunotherapy and a genetic glitch to give cancer patients hope," The Washington Post, 2017, 6 pages.
McGranahan et al., "Clonal neoantigens elicit T cell immunoreactivity and sensitivity to immune checkpoint blockade," Science, Mar. 2016, 351(6280):1463-1469.
Meltzer SJ, Yin J, Manin B, et al. Microsatellite instability occurs frequently and in both diploid and aneuploid cell populations of Barrett's-associated esophageal adenocarcinomas. Cancer research 1994;54:3379-82.
Murphy et al. Comparison of the Microsatellite Instability Analysis System and the Bethesda Panel for Determination of Microsatellite Instability in Colorectal Cancers. J Mol Diagn, Jul. 31, 2006, vol. 8, No. 3 pp. 305-311.
Nakata B, Wang YQ, Yashiro M, et al. Prognostic value of microsatellite instability in resectable pancreatic cancer. Clinical cancer research : an official journal of the American Association for Cancer Research 2002;8:2536-40.
Nishimura et al., "Autoimmune Dilated Cardiomyopathy in PD-1 Receptor-Deficient Mice", Science 2001; 291: 319-22.
Nishimura H, Nose M, Hiai H, Minato N, Honjo T. Development of Lupuslike Autoimmune Diseases by Disruption of the PD-1 Gene Encoding an ITIM MotifCarrying Immunoreceptor. Immunity 1999;11:141-51.
OPDIVO® Label (Dec. 2017).
*OSI Pharmaceuticals, LLC, v. Apotex Inc., Apotex Corp., Apotex Pharmaceuticals Holdings Inc., Apotex Holdings Inc.*, United States Court of Appeals for the Federal Circuit, 2018-1952, dated Oct. 4, 2019, 20 pages.
Palles C, Cazier J-B, Howarth KM, et al. Germline mutations affecting the proofreading domains of POLE and POLO 1 predispose to colorectal adenomas and carcinomas. Nature genetics 2013;45:136-44.
Phillips (British Journal of Surgery, vol. 91, p. 469-475, 2004) (Year: 2004).
Powles T, Eder JP, Fine GD, et al. MPDL3280A (anti-PD-L1) treatment leads to clinical activity in metastatic bladder cancer. Nature 2014;515:558-62.
Rizvi NA, Hellmann MD, Snyder A, et al. Mutational landscape determines sensitivity to PD-1 blockade in non-small cell lung cancer. Science 2015.
Segal NH, Parsons DW, Peggs KS, et al. Epitope landscape in breast and colorectal cancer. Cancer research 2008;68:889-92.
Shaywitz et al., "The Startling History Behind Merck's New Cancer Blockbuster", Forbes, Pharma & Healthcare, 20 pages, 2017.
Sidney Kimmel Comprehensive Cancer Center (Clinical Trial Announcement NCT01876511, published Jun. 12, 2013) (Year: 2013).
Singapore Written Opinion and Search Report issued in Singapore Application No. 11201703541P, dated Nov. 23, 2017, 12 pages.
Smyrk TC, Watson P, Kaul K, Lynch HT. Tumor-infiltrating lymphocytes are a marker for microsatellite instability in colorectal carcinoma. Cancer 2001;91:2417-22.
Snyder A, Makarov V, Merghoub T, et al. Genetic basis for clinical response to CTLA-4 blockade in melanoma. The New England journal of medicine 2014;371:2189-99.
Taube JM, Klein A, Brahmer JR, et al. Association of PD-1, PD-1 ligands, and other features of the tumor immune microenvironment

(56) References Cited

OTHER PUBLICATIONS with response to anti-PD-1 therapy. Clinical cancer research: an official journal of the American Association for Cancer Research 2014;20:5064-74.
The Cancer Genome Atlas Research Network, "Integrated genomic analyses of ovarian carcinoma," Nature, Jun. 2011, 474:609-615.
Timmermann B. Kerick M, Roehr C, et al. Somatic mutation profiles of MSI and MSS colorectal cancer identified by whole exome next generation sequencing and bioinfon:natics analysis. PloS one 2010,5:e15661.
Topalian SL, Hodi FS, Brahmer JR, et al. Safety, activity, and immune correlates of anti-PD-1 antibody in cancer. The New England journal of medicine 2012;366:2443-54.
Topalian SL, Sznol M, McDermott DF, et al. Survival, durable tumor remission, and long-term safety in patients with advanced melanoma receiving nivolumab. Journal of clinical oncology: official journal of the American Society of Clinical Oncology 2014;32:1020-30.
Williams et al., "The analysis of microsatellite instability in extracolonic gastrointestinal malignancy", Pathology 2013; 45: 540-52.
Wolchok JD, Hoos A, O'Day S, et al. Guidelines for the evaluation of immunetherapy activity in solid tumors: immune-related response criteria. Clinical cancer research : an official journal of the American Association for Cancer Research 2009;15:7412-20.
Wolf et al., "UVB-Induced Tumor Heterogeneity Diminishes Immune Response in Melanoma," Cell, 2019, 179(1):219-235.e21.
Yadav et al., "Predicting immunogenic tumour mutations by combining mass spectrometry and exome sequencing", Nature 2014; 515: 572-6.
Yamamoto et al., "Gastrointestinal cancer of the microsatellite mutator phenotype pathway", Journal of gastroenterology 2002; 37: 153-63.
Yarchoan et al., "Tumor mutational burden and response rate to PD-1 inhibition," New England Journal of Medicine, 2017, 377(25):2500-2501.
Young J, Simms LA, Biden KG, et al. Features of colorectal cancers with high-level microsatellite instability occurring in familial and sporadic settings: parallel pathways of tumorigenesis. The American journal of pathology 2001;159:2107-16.
Zhao, Hui et al., 'Mismatch repair deficiency endows tumors with a unique mutation signature and sensitivity to DNA, louble-strand breaks', ELIFE, Aug. 1, 2014, vol. 3 e02725 (internal pp. 1-26).
Brahmer et al., "Survival and long-term follow-up of the phase I trial of nivolumab (Anti-PD-1; BMS-936558; ONO-4538) in patients (pts) with previously treated advanced non-small cell lung cancer (NSCLC)," J Clin Oncol., 2013, 31(suppl 15) abstr 8030.
Drake et al., "Mechanisms of immune evasion by tumors," Adv Immunol., 2006, 90:51-81.
Extended European Search Report in European Appln. No. 21175020.3, dated Aug. 9, 2021, 11 pages.
Lyford-Pike et al., "Evidence for a role of the PD-1:PD-L1 pathway in immune resistance of HPV-associated head and neck squamous cell carcinoma," Cancer Res. 2013;73:1733-1741.
Pardoll et al., "The blockade of immune checkpoints in cancer immunotherapy," Nat Rev Cancer, 2012, 12 : 252-64.
Taube et al., "Colocalization of inflammatory response with B7-H1 expression in human melanocytic lesions supports an adaptive resistance mechanism of immune escape," .Science Transl Med., 2012,4:127ra37-127ra37.
Taube, "Emerging immunologic biomarkers: Setting the [TNM-immune] stage," Clin Cancer Res., 2014, 20:8:2023-2025.
Topalian et al., "Targeting the PD-1/B7-H1(PD-L1) pathway to activate anti-tumor immunity," Curr Opin Immunol. 2012;24:207-212.
Topalian et al., "Cancer immunotherapy comes of age," J Clin Oncol. 2011; 29:4828-4836.
Vogelstein et al., "Cancer genome landscapes," Cancer genome landscapes, Sci. 2013, 339:1546-58.
Wang et al.," In vitro characterization of the anti-pd-1 antibody nivolumab bms-936558, and in vivo toxicology in non-human primates," Cancer immunology Res., May 2014, 2:9:846-856.
Clinical Trials Identifier: NCT01876511, "Phase 2 Study of MK-3475 in Patients With Microsatellite Unstable (MSI) Tumors", Version 1, Jun. 10, 2013, 7 pages.
Clinical Trials Identifier: NCT01876511, "Phase 2 Study of MK-3475 in Patients With Microsatellite Unstable (MSI) Tumors", Version 10, Apr. 15, 2015, 8 pages.
Clinical Trials Identifier: NCT01876511, "Phase 2 Study of MK-3475 in Patients With Microsatellite Unstable (MSI) Tumors", Version 11, Jun. 9, 2015, 9 pages.
Clinical Trials Identifier: NCT01876511, "Phase 2 Study of MK-3475 in Patients With Microsatellite Unstable (MSI) Tumors", Version 2, Jun. 12, 2013, 7 pages.
Clinical Trials Identifier: NCT01876511, "Phase 2 Study of MK-3475 in Patients With Microsatellite Unstable (MSI) Tumors", Version 3, Sep. 20, 2013, 7 pages.
Clinical Trials Identifier: NCT01876511, "Phase 2 Study of MK-3475 in Patients With Microsatellite Unstable (MSI) Tumors", Version 4, May 21, 2014, 7 pages.
Clinical Trials Identifier: NCT01876511, "Phase 2 Study of MK-3475 in Patients With Microsatellite Unstable (MSI) Tumors", Version 5, Jun. 25, 2014, 7 pages.
Clinical Trials Identifier: NCT01876511, "Phase 2 Study of MK-3475 in Patients With Microsatellite Unstable (MSI) Tumors", Version 6, Sep. 15, 2014, 7 pages.
Clinical Trials Identifier: NCT01876511, "Phase 2 Study of MK-3475 in Patients With Microsatellite Unstable (MSI) Tumors", Version 7, Dec. 26, 2014, 7 pages.
Clinical Trials Identifier: NCT01876511, "Phase 2 Study of MK-3475 in Patients With Microsatellite Unstable (MSI) Tumors", Version 8, Jan. 29, 2015, 7 pages.
Clinical Trials Identifier: NCT01876511, "Phase 2 Study of MK-3475 in Patients With Microsatellite Unstable (MSI) Tumors", Version 9, Feb. 26, 2015, 8 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 1, Feb. 10, 2014,9 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 10, Jun. 25, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 11, Jul. 9, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 12, Jul. 23, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 13, Aug. 11, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 14, Aug. 28, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 15, Sep. 15, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 16, Oct. 13, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 17, Oct. 30, 2014, 12 pages.

(56) References Cited

OTHER PUBLICATIONS

Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 18, Nov. 13, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 19, Nov. 20, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 2, Mar. 25, 2014, 11 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 20, Dec. 5, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 21, Dec. 31, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 22, Jan. 27, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 23, Feb. 6, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 24, Feb. 19, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 25, Mar. 5, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 26, Mar. 23, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 27, Apr. 13, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 28, Apr. 20, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 29, Jun. 3, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 3, Mar. 28, 2014, 11 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 30, Jun. 4, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 31, Jun. 22, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 32, Jul. 3, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 33, Jul. 17, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 34 Aug. 6, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 35, Sep. 3, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 36, Sep. 16, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 37, Oct. 15, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 38, Nov. 4, 2015, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 4, Apr. 29, 2014, 11 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 5, May 2, 2014, 11 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 6, May 7, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 7, May 27, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 8, May 30, 2014, 12 pages.
Clinical Trials Identifier: NCT2060188, "A Phase 2 Clinical Trial of Nivolumab and Nivolumab Plus Ipilimumab in Recurrent and Metastatic Microsatellite High (MSI-H) Colon Cancer", Version 9, Jun. 12, 2014, 12 pages.
Kroemer et al., "Colorectal cancer: the first neoplasia found to be under immunosurveillance and the last one to respond to immunotherapy?," Oncoimmunology, Jun. 2015, 4:7:e1058597.
Maby et al., "Correlation between Density of CD8+ T-cell Infiltrate in Microsatellite Unstable Colorectal Cancers and Frameshift Mutations: A Rationale for Personalized Immunotherapy," Cancer Res., Sep. 2015, 75:17:3446-55.
Sunakawa et al., "Molecular classification of gastric adenocarcinoma: translating new insights from the cancer genome atlas research network," Curr. Treat Options Oncol., Apr. 2015, 4:17.
Tumeh et al., "PD-1 blockade induces responses by inhibiting adaptive immune resistance," Nat., Nov. 2017, 515:7528:568-571.
Xiao et al., "The microsatellite instable subset of colorectal cancer is a particularly good candidate for checkpoint blockade immunotherapy," Cancer Discov., Jan. 2015, 5:1:16-8.
Lipson et al, Durable Cancer Regression Off-Treatment and Effective Reinduction Therapy with an Anti PD 1 Antibody.†
Dung et al, Phase 2 study of programmed death 1 antibody anti PD 1, MK 3475 in patients with microsatellite unstable MSI tumors.†
Gatalica et al, Programmed Cell Death 1 PD 1 and Its Ligand PD L1 in Common Cancers and Their Correlation with Molecular Cancer Type.†
Zeynep Eroglu, Checkpoint Inhibition of PD 1 the Promise of Pembrolizumab (MK 3475) and Beyond.†

(56) References Cited

OTHER PUBLICATIONS

Sidney Kimmel Comprehensive Cancer Center at John Hopkins, Phase 2 Study of MK 3475 in Patients with Microsatellite Unstable (MSI) Tumors.†

Durie et al, Retrospective review of colorectal cancer specimens in individuals younger than age 50 for microsatellite instability testing and DNA mismatch repair enzyme expression.†

Cho et al, Clinicopathologic characteristics of microsatellite instability MSI tumors in resected gastric cancer patients.†

Llosa et al, Immune checkpoints expression in MSI versus MSS colorectal cancers and their potential therapeutic implications.†

Bacher et al, Development of a fluorescent multiplex assay for detection of MSI High tumors.†

Nazneen Rahman, Mainstreaming genetic testing of cancer predisposition genes.†

\* cited by examiner
† cited by third party

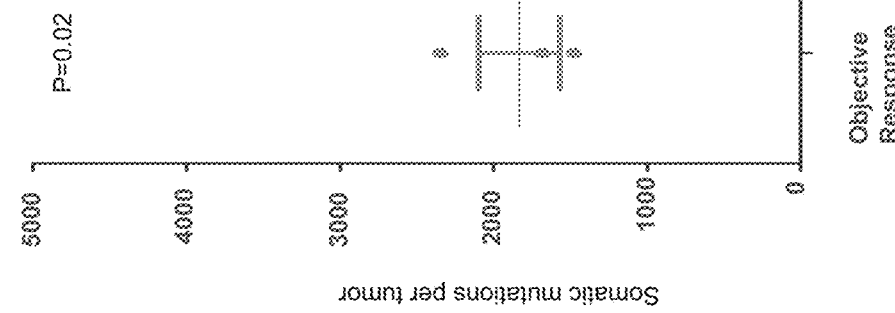
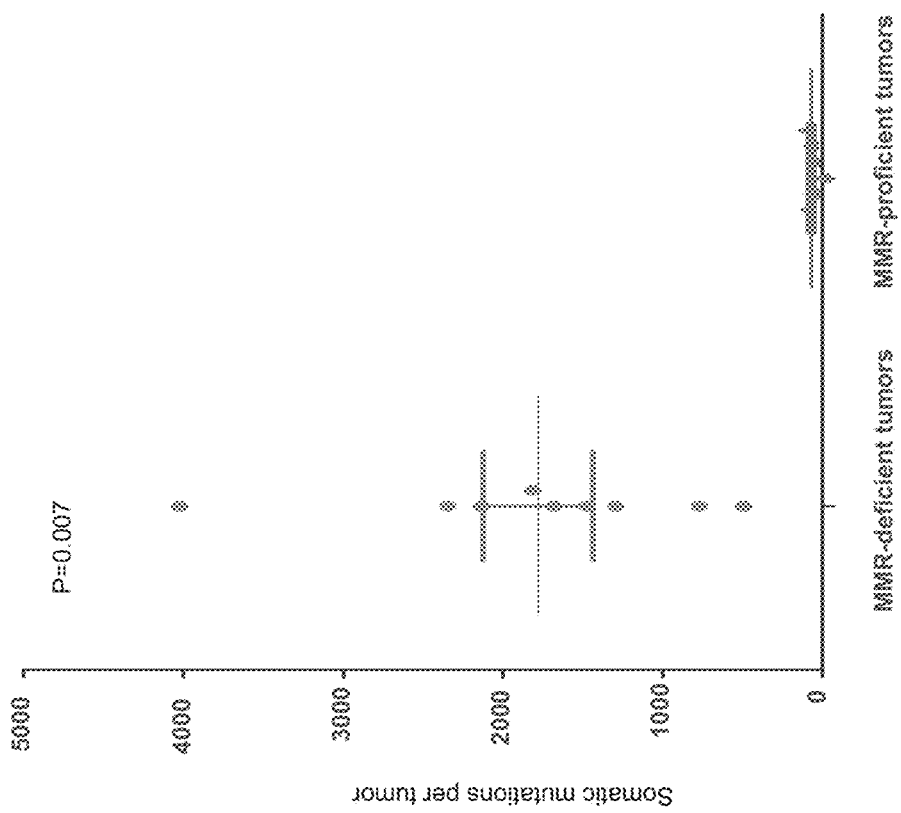

Fig. 10. Comparison of immune-related and RECIST response criteria

| | CR | PR | SD | PD |
|---|---|---|---|---|
| RECIST 1.1 | All lesions gone | > 30% decrease in sum of target lesion diameters from baseline | Neither PR or PD from nadir | > 20% increase in sum of target lesion diameters from nadir<br><br>Appearance of new lesion |

| | irCR | irPR | irSD | irPD |
|---|---|---|---|---|
| irRC | All lesions gone<br><br>New lesions allowed | SPD of index + any new lesions decreases >50% from baseline<br><br>New lesions allowed | SPD of index + any new lesions neither irCR, irPR, or irPD<br><br>CR, P<br><br>New lesions allowed | SPD of index + any new lesions increases > 25% from nadir<br><br>irPD is based on SPD only |

RECIST 1.1 = Response Evaluation Criteria in Solid Tumors 1.1; irRC= Immune Related Response Criteria
CR= complete response; PR= paritial response; SD= stable disease; PD= progressive disease; SPD= sum of the product of the perpindicular diameters Fig. 11. Immune-related response to treatment

| Type of immune-related responses-no (%) | MMR-deficient CRC n=10 | MMR-proficient CRC n=18 | MMR-deficient non-CRC n=7 |
|---|---|---|---|
| Complete Response | 0 (0) | 0 (0) | 1 (14)[1] |
| Partial Response | 4 (40) | 0 (0) | 4 (57)[2] |
| Stable Disease (Week 12) | 5 (50) | 2 (11) | 0 (0) |
| Progressive Disease | 1 (10) | 11 (61) | 2 (29) |
| Not Evaluable[3] | 0 (0) | 5 (28) | 0 (0) |
| Immune-related objective response rate (%) | 40 | 0 | 71 |
| 95% CI | 12-74 | 0-19 | 29-96 |
| Immune-related disease control rate (%)[4] | 90 | 11 | 71 |
| 95% CI | 55-100 | 1-35 | 29-96 |
| Immune-related PFS at 20 weeks (%) | 78 | 11 | 67 |
| 95% CI | 40-97 | 1-35 | 22-96 |

[1] Originally PR at 12 that was converted to CR at 20 weeks
[2] One PR at 12 weeks
[3] Patients were considered not evaluable if they did not undergo a 12 week scan due to clinical progression. [4]The rate of disease control was defined as the percentage of patients who had a complete response, partial response or stable disease for 12 weeks or more.

Fig. 12. Correlation of total somatic mutations and mutation associated neoantigens (MANA) with clinical outcomes

Trend test to compare CR/PR vs. SD vs. PD

| Variable | P value |
|---|---|
| Total Somatic Mutations | 0.024 |
| Mutation-associated neoantigens (MANAs) | 0.028 |

Association of mutations and MANA with response rates

| scale*) | Odds Ratio | 95% Confidence interval Variable (log | | P value |
|---|---|---|---|---|
| | | Lower | Upper | |
| Total Somatic Mutations | 3.312 | 0.500 | 21.924 | 0.214 |
| Mutation-associated neoantigens (MANAs) | 3.087 | 0.617 | 15.439 | 0.170 |

Association of mutations and MANA with PFS

| Variable (log scale*) | Hazard Ratio | 95% Confidence Interval | | P value |
|---|---|---|---|---|
| | | Lower | Upper | |
| Total Somatic Mutations | 0.628 | 0.424 | 0.931 | 0.021 |
| Mutation-associated neoantigens (MANAs) | 0.599 | 0.391 | 0.916 | 0.018 |

Association of mutations and MANA with OS

| Variable (log scale*) | Hazard Ratio | 95% Confidence interval | | P value |
|---|---|---|---|---|
| | | Lower | Upper | |
| Total Somatic Mutations | 0.707 | 0.481 | 1.038 | 0.077 |
| Mutation-associated neoantigens (MANAs) | 0.676 | 0.453 | 1.008 | 0.055 |

Fig. 13. Correlation of immune markers with clinical outcome

Trend test to compare CR/PR vs. SD vs. PD

| Variable | P value |
|---|---|
| PD-L1 membranous expression within tumor (>5% vs. <5%) | 0.208 |
| PD-L1 expression by TIL and associated macrophages at invasive front (%) | 0.043 |
| PD-L1 expression by TIL and associated macrophages on TILS within tumor (%) | 0.024 |
| CD8 density (cells/mm2) within tumor | 0.017 |
| CD8 density (cells/mm2) at invasive front | 0.768 |
| CD8 density (cells/mm2) in non-tumor tissue | 0.346 |

* except for PD-L1 Expression on Tumor (>5% vs. <5%), which is represented as a binary variable

Association of immune markers with response rates

| Variable (log scale*) | Odds Ratio | 95% Confidence interval Lower | 95% Confidence interval Upper | P value |
|---|---|---|---|---|
| PD-L1 membranous expression within tumor (>5% vs. <5%) | 3.200 | 0.354 | 28.945 | 0.301 |
| PD-L1 expression by TIL and associated macrophages at invasive front (%) | 1.075 | 0.820 | 1.411 | 0.600 |
| PD-L1 expression by TIL and associated macrophages on TILS within tumor (%) | 1.139 | 0.862 | 1.506 | 0.361 |
| CD8 density (cells/mm2) within tumor | 1.337 | 0.708 | 2.531 | 0.372 |
| CD8 density (cells/mm2) at invasive front | 0.515 | 0.193 | 1.374 | 0.185 |
| CD8 density (cells/mm2) in non-tumor tissue | 1.219 | 0.535 | 2.777 | 0.637 |

* except for PD-L1 Expression on Tumor (>5% vs. <5%), which is represented as a binary variable

Association of immune markers with PFS

| Variable (log scale*) | Hazard Ratio | 95% Confidence interval Lower | 95% Confidence interval Upper | P value |
|---|---|---|---|---|
| PD-L1 membranous expression within tumor (>5% vs. <5%) | 0.196 | 0.025 | 1.518 | 0.119 |
| PD-L1 expression by TIL and associated macrophages at invasive front (%) | 0.899 | 0.784 | 1.031 | 0.126 |
| PD-L1 expression by TIL and associated macrophages on TILS within tumor (%) | 0.888 | 0.765 | 1.031 | 0.118 |
| CD8 density (cells/mm2) within tumor | 0.900 | 0.794 | 1.020 | 0.100 |
| CD8 density (cells/mm2) at invasive front | 1.017 | 0.607 | 1.706 | 0.948 |
| CD8 density (cells/mm2) in non-tumor tissue | 1.144 | 0.780 | 1.677 | 0.492 |

* except for PD-L1 Expression on Tumor (>5% vs. <5%), which is represented as a binary variable

Association of immune markers with OS

| Variable (log scale*) | Hazard Ratio | 95% Confidence interval Lower | 95% Confidence interval Upper | P value |
|---|---|---|---|---|
| PD-L1 membranous expression within tumor (>5% vs. <5%) | 0.513 | 0.062 | 4.232 | 0.535 |
| PD-L1 expression by TIL and associated macrophages at invasive front (%) | 0.978 | 0.816 | 1.173 | 0.813 |
| PD-L1 expression by TIL and associated macrophages on TILS within tumor (%) | 0.931 | 0.762 | 1.136 | 0.487 |
| CD8 density (cells/mm2) within tumor | 0.918 | 0.813 | 1.036 | 0.167 |
| CD8 density (cells/mm2) at invasive front | 0.986 | 0.502 | 1.934 | 0.967 |
| CD8 density (cells/mm2) in non-tumor tissue | 1.018 | 0.635 | 1.631 | 0.941 |

* except for PD-L1 Expression on Tumor (>5% vs. <5%), which is represented as a binary variable

CHECKPOINT BLOCKADE AND MICROSATELLITE INSTABILITY

CROSS REFERENCE TO RELATED APPLICATIONS

This application is a continuation of U.S. application Ser. No. 16/144,549, filed Sep. 27, 2018, now U.S. Pat. No. 10,934,356, issued on Mar. 2, 2021, which is a continuation of U.S. application Ser. No. 15/523,451, filed May 1, 2017, which is a National Stage application under 35 U.S.C. § 371 of International Application No. PCT/US2015/060331, having an International Filing Date of Nov. 12, 2015, which claims the benefit of priority of U.S. Provisional Application No. 62/190,977, filed Jul. 10, 2015 and U.S. Provisional Application No. 62/079,357, filed Nov. 13, 2014, each of which are incorporated herein by reference in their entirety.

This invention was made with government support under grants CA043460 and CA062924 awarded by the National Institutes of Health. The government has certain rights in the invention.

TECHNICAL FIELD OF THE INVENTION

This invention is related to the area of cancer. In particular, it relates to cancer therapy.

BACKGROUND OF THE INVENTION

Microsatellite instability (MSI) is the accumulation of sequencing errors in microsatellites. This occurs in tumors with deficiency in DNA mismatch repair. MSI is present in Lynch Syndrome which is an inherited cancer syndrome that predisposes patients to colon, endometrial, gastric cancer, ovarian, small intestine, liver, hepatobiliary, upper urinary tract, brain, and prostate cancer. MSI is also present in 10-20% of sporadic colorectal, gastric, prostate, lung, ampullary, and endometrial cancers. Between 0.3% and 13% of pancreatic cancers are reported to be MSI as well.

The importance of intact immune surveillance in controlling outgrowth of neoplastic transformation has been known for decades. Accumulating evidence shows a correlation between tumor-infiltrating lymphocytes (TILs) in cancer tissue and favorable prognosis in various malignancies. In particular, the presence of CD8+ T-cells and the ratio of CD8+ effector T-cells/FoxP3+ regulatory T-cells seems to correlate with improved prognosis and long-term survival in solid malignancies such as ovarian, colorectal and pancreatic cancer, hepatocellular carcinoma, malignant MEL and RCC. TILs can be expanded ex vivo and re-infused, inducing durable objective tumor responses in cancers such as melanoma.

The PD-1 receptor-ligand interaction is a major pathway hijacked by tumors to suppress immune control. The normal function of PD-1, expressed on the cell surface of activated T-cells under healthy conditions, is to down-modulate unwanted or excessive immune responses, including autoimmune reactions. The ligands for PD- 1 (PD-L1 and PD-L2) are constitutively expressed or can be induced in various tumors. Binding of either PD-1 ligand to PD-1 inhibits T-cell activation triggered through the T-cell receptor. PD-L1 is expressed at low levels on various non-hematopoietic tissues, most notably on vascular endothelium, whereas PD-L2 protein is only detectably expressed on antigen-presenting cells found in lymphoid tissue or chronic inflammatory environments. PD-L2 is thought to control immune T-cell activation in lymphoid organs, whereas PD-L 1 serves to dampen unwarranted T-cell function in peripheral tissues. Although healthy organs express little (if any) PD-L1, a variety of cancers were demonstrated to express abundant levels of this T-cell inhibitor. High expression of PD-L1 on tumor cells (and to a lesser extent of PD-L2) has been found to correlate with poor prognosis and survival in various cancer types, including renal cell carcinoma (RCC), pancreatic carcinoma, hepatocellular carcinoma, ovarian carcinoma and non-small cell lung cancer (NSCLC). Furthermore, PD-1 has been suggested to regulate tumor-specific T cell expansion in patients with malignant MEL The observed correlation of clinical prognosis with PD-L1 expression in multiple cancers suggests that the PD-1/PD-L1 pathway plays a critical role in tumor immune evasion and should be considered as an attractive target for therapeutic intervention.

Blockade of immune checkpoints such as cytotoxic T-lymphocyte antigen-4 (CTLA- 4) and programmed death-1 (PD-1) is showing promise in patients with cancer. CTLA-4 and PD-1 are upregulated on activated T cells and provide inhibitory signals to T cells undergoing activation. Inhibitory antibodies directed at these receptors have been shown to break immune tolerance and promote anti-tumor immunity. MK-3475 is a humanized monoclonal IgG4 antibody against PD-1 and is showing activity in multiple tumor types including melanoma and non-small cell lung cancer (NSCLC). Previously, activity of a different PD-1 blocking antibody, BMS-936558, a fully humanized monoclonal IgG4 antibody, also showed activity in melanoma, NSCLC, and a complete response in a single patient with colorectal cancer.

MK-3475 (previously known as SCH 900475) is a potent and highly-selective humanized mAb of the IgG4/kappa isotype designed to directly block the interaction between PD-1 and its ligands, PD-L1 and PD-L2. MK-3475 contains the S228P stabilizing mutation and has no antibody-dependent cell-mediated cytotoxicity (ADCC) or complement-dependent cytotoxicity (CDC) activity. MK-3475 strongly enhances T lymphocyte immune responses in cultured blood cells from healthy human donors, cancer patients, and primates. In T- cell activation assays using human donor blood cells, the EC50 was in the range of 0.1 to 0.3 nM. MK-3475 also modulates the level of interleukin-2 (IL-2), tumor necrosis factor alpha (TNFα), interferon gamma (IFNγ), and other cytokines. The antibody potentiates existing immune responses only in the presence of antigen and does not nonspecifically activate T-cells.

The programmed death 1 (PD-1) pathway is a negative feedback system repressing Thl cytotoxic immune responses that, if unregulated, could damage the hose[1-3]. It is upregulated in many tumors and their surrounding microenvironment. Blockade of this pathway with antibodies to PD-1 or its ligands has led to remarkable clinical responses in some patients with many different cancer types, including melanomas, non-small cell lung cancer, renal cell carcinoma, bladder cancer and Hodgkin's lymphoma[4-10]. The expression of ligands to PD-1 (PD-L1 or PD-L2) on the surface of tumor cells or immune cells is important but not a definitive predictive biomarker for response to PD-1 blockade[4,6-8,11].

We were intrigued that, in reports of the effects of PD-1 blockade in human tumors, only one of 33 colorectal cancer (CRC) patients responded to this treatment, in contrast to substantial fractions of patients with melanomas, renal cell cancers, and lung tumors.[10,12] What was different about this single patient? We hypothesized that this patient had MMR-deficiency, because MMR-deficiency occurs in a small fraction of advanced CRCs,[13,14] somatic mutations found in tumors can be recognized by the patient's own immune system,[15] and MMR-deficient cancers have 10- to 100-fold more somatic mutations than MMR-proficient CRC.[16-18] Moreover, MMR-deficient cancers contain prominent lymphocyte infiltrates, consistent with an immune response[19-22]. And two of the tumor types that were most responsive to PD-1 blockade in a study by Topalian et al.[10] had high numbers of somatic mutations as a result of exposure to cigarette smoke (lung cancers) or UV radiation (melanomas)[23,24]. Our hypothesis was correct: the tumor of the single CRC patient who responded to PD-1 blockade was MMR-deficient[25]. We therefore hypothesized that MMR-deficient tumors are more responsive to PD-1 blockade than are MMR-proficient tumors.

To test this hypothesis, we initiated a phase 2 clinical trial to evaluate immune checkpoint blockade in patients whose tumors had or did not have MMR-deficiency. Since MMR deficiency in tumors arises through two routes[26-28], we recruited patients with Hereditary Non-Polyposis Colorectal Cancer (HNPCC, also known as Lynch Syndrome), which results from an inherited germline defect in one of four MMR genes followed by a second inactivating somatic change in the remaining wild-type allele. We also recruited patients with sporadic MMR-deficient tumors, where both alleles of a MMR gene are inactivated by somatic mutations or by epigenetic silencing[29]. In either case, the neoplasms that arise harbor hundreds or thousands of mutations[16,18].

There is a continuing need in the art to improve cancer treatments so that the lives of patients are not curtailed and so that the quality of life is not diminished.

SUMMARY OF THE INVENTION

According to one embodiment of the invention a method of treating a cancer patient is provided. The cancer patient has a high mutational burden, such as found in microsatellite instable cancer (MSI). An immune checkpoint inhibitory antibody is administered to the cancer patient.

According to another embodiment of the invention a method of treating a cancer patient is provided. A sample from a cancer patient is tested for one or more microsatellite markers selected from the group consisting of BAT-25, BAT-26, MON0-27, NR-21, NR-24, Penta C, and Penta D, and determined to have microsatellite instability. The cancer is selected from the group consisting of: colon, gastric, endometrial, cholangiocarcinoma, pancreatic, and prostate cancers. An anti-PD-1 antibody is administered to the cancer patient.

According to another embodiment of the invention a method is provided for categorizing a tumor of a human. A sample from the human is tested to evaluate stability of one or more microsatellite markers. Microsatellite instability is determined in the sample. The tumor is identified as a good candidate for treatment with an immune checkpoint inhibitory antibody.

According to yet another embodiment of the invention a method is provided for categorizing a tumor of a human. A sample from the human is tested to evaluate stability of one or more microsatellite markers. Microsatellite stability in the sample is determined. The tumor is identified as a bad candidate for treatment with an immune checkpoint inhibitory antibody.

These and other embodiments which will be apparent to those of skill in the art upon reading the specification provide the art with methods for treating microsatellite instable cancers.

BRIEF DESCRIPTION OF THE DRAWINGS

(FIG. 1A) Biochemical Responses. Serum protein biomarker levels were measured with each cycle and the values represent percent change from baseline. Patients were included if baseline tumor marker values were greater than the upper limit of normal. CA-125 was used for a patient with endometrial cancer; CA19-9 was used for one cholangiocarcinoma and one ampullary cancer; and CEA was used for all other patients. Green, red, and black lines represent patients with MMR-deficient CRCs, MMR-proficient CRCs, and MMR-deficient non-CRC, respectively. (FIG. 1B) Radiographic responses. Tumor responses were measured at regular intervals and values show the best fractional change of the sum of longest diameters (SLD) from the baseline measurements of each measurable tumor.

FIGS. 6A-6B (FIG. S5.) Somatic mutations in MMR-deficient and proficient tumors. Total somatic mutations per tumor identified by exome sequencing of tumor and matched normal DNA (FIG. 6A) and correlation with objective responses (FIG. 6B) (non-parametric Wilcoxon test, p=0.007 and Jonckheere-Terpstra test for trend, p=0.02).

FIG. 10 (Table S 1.) Comparison of immune-related and RECIST response criteria (adapted from Wolchok et al. Clin Can Res 2009;15:7412-20.)

FIG. 11 (Table S2.) Immune-Related response to treatment

FIG. 12 (Table S4.) Correlation of total somatic mutations and mutation associated neoantigens (MANA) with clinical outcomes FIG. 13 (Table S5.) Correlation of immune markers with clinical outcome

DETAILED DESCRIPTION OF THE INVENTION

Figures 1A, 1B:
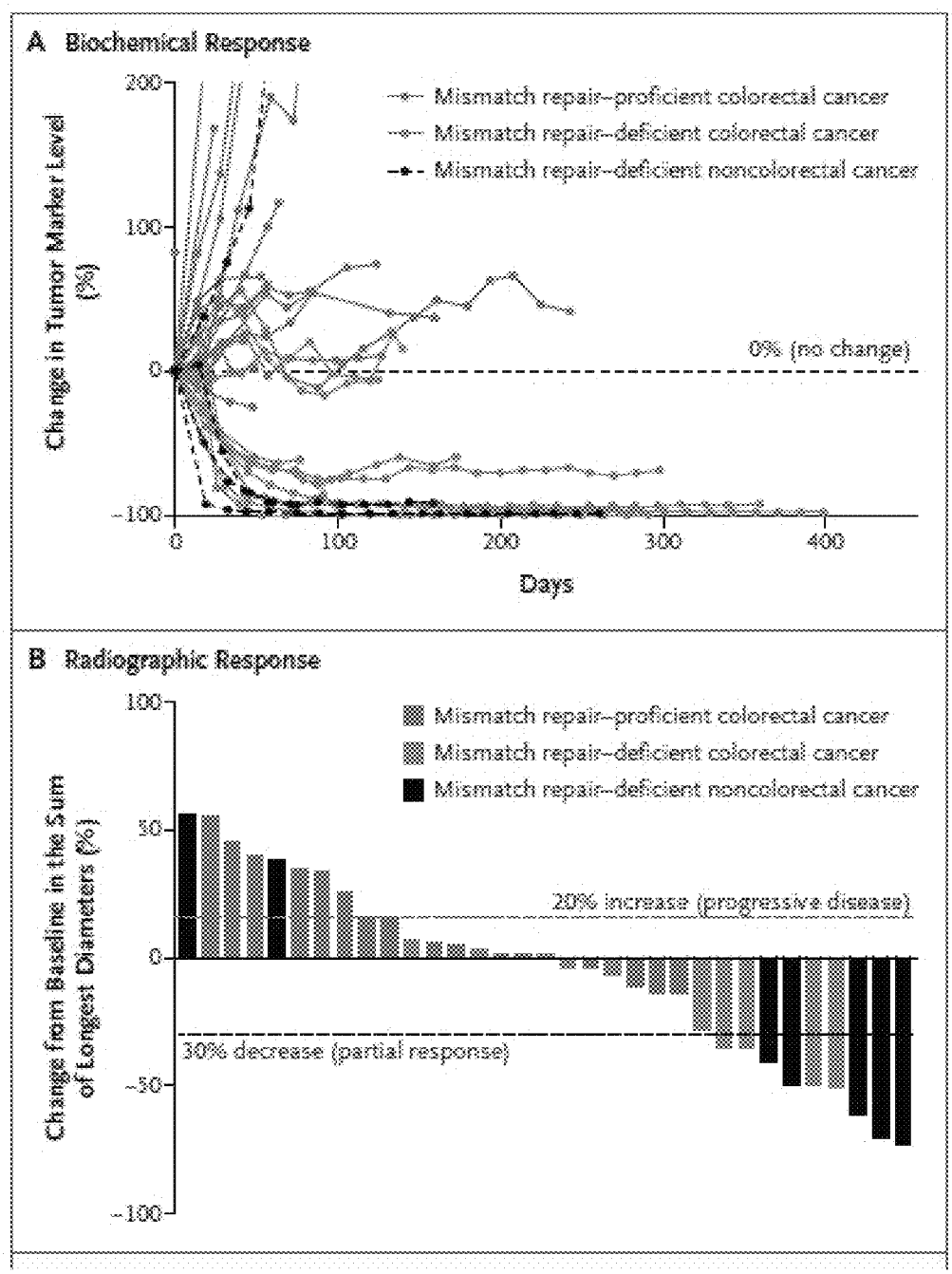
FIGS. 1A-1B. Clinical Responses to pembrolizumab.

The inventors have found that immune checkpoint inhibitors work best in tumors with high mutation burdens. Furthermore, tumors deficient in mismatch repair are particularly susceptible to a particular form of immunotherapy because this phenotype results in ongoing accumulation of mutations at a high frequency. The inventors have developed a treatment for cancer patients that display the microsatellite instability phenotype or other high mutational burden. The treatment involves an inhibitory antibody for an immune checkpoint. Such checkpoints include PD-1, IDO, CTLA-4, PD-L1, and LAG-3. Other immune checkpoints can be used as well. Antibodies can be administered by any means that is convenient, including but not limited to intravenous infusion, oral administration, subcutaneous administration, sublingual administration, ocular administration, nasal administration, etc.

Microsatellite instability (MSI) tumors are deficient in DNA mismatch repair which leads to a high rate of spontaneous mutations and the potential for the expression of neo-antigens. Furthermore, similar to melanoma, in MSI positive colon cancers, there is often prominent lymphocyte infiltration. Any tumors that are MSI or otherwise high mutational burden may be treated according to the invention. They may be tested for the attribute of MSI according to any method known in the art, including but not limited that described in example 1 below. Any of one or more MSI markers can be tested to determine an MSI phenotype. Samples may be tested for high mutational burden by identifying tumors with at least 100, at least 200, at least 300, at least 400, at least 500, at least 600, at least 700, at least 800, at least 900, at least 1000, at least 1100, at least 1200, at least 1300, at least 1400, at least 1500, or at least 1600 mutations per tumor genome. High mutational burden means a large number of somatic mutations in the tumor relative to normal tissues of the individual. An average number of somatic mutations in a non-MSI tumor is about 70 somatic mutations.

Any type of tumor that displays the MSI phenotype or a high mutational burden may be tested and/or treated according to the invention. These include without limitation cancers of the colon, gastric, endometrial, cholangiocarcinoma, pancreatic, and prostate cancer. Tumors of the ampulla, biliary, brain, including glioma, breast, lung, skin, esophagus, liver, kidney, ovaries, sarcoma, uterus, cervix, bladder, testes, oral cavity, tongue, and small and large bowel may also be tested and/or treated.

Testing of MSI can be accomplished by any means known in the art. One or more of the following markers may be tested: five nearly monomorphic mononucleotide repeat markers (BAT-25, BAT-26, MONO-27, NR-21 and NR-24) and two highly polymorphic pentanucleotide repeat markers (Penta C and Penta D). In one commercial system which can be used, fluorescently labeled primers (marker panel) are used for co-amplification of all seven of the above named markers. Fragments are detected after amplification for assignment of genotype/phenotype.

Samples that can be tested for MSI include tumor tissue as well as body fluids that contain nucleic acids shed from tumors. Testing for tumor DNA in such tissues and body fluids is well known.

Types of antibodies which can be used include any that are developed for the immune checkpoint inhibitors. These can be monoclonal or polyclonal. They may be single chain fragments or other fragments of full antibodies, including those made by enzymatic cleavage or recombinant DNA techniques. They may be of any isotype, including but not limited to IgG, IgM, IgE. The antibodies may be of any species source, including human, goat, rabbit, mouse, cow, chimpanzee. The antibodies may be humanized or chimeric. The antibodies may be conjugated or engineered to be attached to another moiety, whether a therapeutic molecule or a tracer molecule. The therapeutic molecule may be a toxin, for example.

The data from the small phase 2 trial of pembrolizumab to treat tumors with and without deficiency of MMR supports the hypothesis that MMR-deficient tumors are more responsive to PD-1 blockade than are MMR-proficient tumors. MMR-deficiency occurs in many cancers, including those of the colorectum, uterus, stomach, biliary tract, pancreas, ovary, prostate and small intestine[18,34-42]. Patients with MMR-deficient tumors of these types also benefit from anti-PD-1 therapy, as may patients whose tumors contain other DNA repair deficiencies, such as those with mutations in POLD, POLE, or MYH.[18,43,44]

The hypothesis that MMR-deficient tumors stimulate the immune system is not a new idea[45], and has been supported by the dense immune infiltration and Th1-associated cytokine-rich environment observed in MMR-deficient tumors.[19-22,46] A recent study refined these classic observations by showing that the MMR-deficient tumor microenvironment strongly expressed several immune checkpoint ligands including PD-1, PD-L1, CTLA-4, LAG-3 and IDO, indicating that their active immune microenvironment is counterbalanced by immune inhibitory signals that resists tumor elimination[47]. That the immune infiltrate associated with MMR-deficient carcinomas was directed at neoantigens was the most likely explanation for both the old and new findings. The correlation of higher mutational load and higher response rate to anti-CTLA-4 in melanoma[41] and anti-PD-1 in lung cancer[48] provide further support for the idea that MANA recognition is an important component of the endogenous anti-tumor immune response.

Based on the results of the current and previous studies, we suggest that the greatly (>20-fold) increased number of mutation-associated neoantigens resulting from MMR deficiency (FIG. 12 (Table S4); also available on line at New England Journal of Medicine; incorporated by reference herein) is the basis for the enhanced anti-PD-1 responsiveness of this genetically defined subset of cancers. Though our estimates for the number of mutation-associated neoantigens in tumors is based only on in silico predictions of binding-affinity, this suggestion is consistent with the observation that MMR-proficient tumors have far less infiltration of lymphocytes than MMR-deficient tumors (FIG. 7 (S6), FIG. 8 (S7) and FIG. 13 (Table S5); available on line at New England Journal of Medicine; incorporated by reference herein). Recent studies[49,50] show that only a tiny proportion of predicted neo-epitopes are actually presented on the cell surface with MHC and are targets of endogenous T cell responses. It seems likely, though that the number of predicted mutation-associated neoantigens is proportionate to the number of actual mutation-associated neoantigens, and tumors with a high number of actual mutation-associated neoantigens are more likely to stimulate the immune system to react against the tumor. Alternative mechanisms underlying the difference in anti-PD-1 responsiveness between MMR-deficient and MMR-proficient tumors should also be considered. For example, different signaling pathways activated in MMR-deficient and MMR-proficient tumors may result in differences in secretion of soluble factors that could result in differential activation of the PD-1 pathway within the tumor microenvironment[26-28]. Genetic differences could effect epigenetic differences that alter the expression of tumor-associated self-antigens that in turn could alter the antigenicity of the tumor. Experimental analyses of antigen-specific immune responses as well as changes in immune microenvironments should help to define the relative contribution of these factors to the striking responsiveness of MMR-deficient tumors to PD-1 antibodies.

Several notable observations were made during the course of this study. First, changes in serum protein biomarkers, like CEA, corresponded with clinical benefit after a single dose of therapy. Declines in CEA levels preceded objective radiographic evidence by several months; perhaps other biomarkers such as circulating tumor DNA (ctDNA) may also be beneficial as surrogate markers of early response.[51,52] Second, our results suggest that the evaluation of tumor genomes can help guide immunotherapy. They support the view that the number and type of alterations may prove useful for judging the potential utility of immune checkpoint inhibitors, even in MMR-proficient cancers[41,48,53] Most importantly, our results demonstrate a new approach for the treatment of a specific class of tumors based solely on genetic status: i.e., without regard to underlying tumor type.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

MSI Testing

MSI testing is already standardized and performed in CLIA-certified laboratories without need for assay development. Archived tumor samples or newly obtained biopsies will be used for determining MSI. MSI status will be performed locally by CLIA certified immunohistochemistry (IHC) or PCR based tests for eligibility. Evaluable patients will be confirmed using the MSI Analysis System from Promega at Johns Hopkins. This test will determine MSI status through the insertion or deletion of repeating units in the five nearly monomorphic mononucleotide repeat markers (BAT-25, BAT-26, MONO-27, NR-21 and NR-24). At least 2 MSI loci are required to be evaluable in Cohorts A and C. Patients may be assigned to a new cohort and/or replaced based on the Promega test results.

EXAMPLE 2

Methods
Patients
Treatment-refractory progressive metastatic cancer patients for this phase 2 study were recruited from three participating centers (Table 1). Three cohorts were evaluated: Cohort A was composed of patients with MMR-deficient colorectal adenocarcinomas; Cohort B was composed of patients with MMR-proficient colorectal adenocarcinomas; and Cohort C was composed of patients with MMR-deficient cancers of types other than colorectal.
Study Oversight
The protocol, which can be found at NEJM.org, was approved by each site's institutional review boards, and the study was conducted in accordance with the Declaration of Helsinki and the International Conference on Harmonization Guidelines for Good Clinical Practice. All the patients provided written informed consent before study entry. The principal investigator (D.L.) and study sponsor (L.A.D.) were responsible for oversight of the study. Merck donated the study drug, reviewed the final drafts of the protocol and of this manuscript. The clinical study was primarily funded through philanthropic support.
Study Design
This phase 2 trial was conducted using a Green-Dahlberg two-stage design and consisted of the three parallel cohorts described above. The study agent, pembrolizumab (Merck), was administered at 10 mg/kg intravenously every 14 days. Pembrolizumab is a humanized monoclonal anti-PD-1 antibody of the IgG4/kappa isotype that blocks the interaction between PD-1 and its ligands, PD-L1 and PD-L2.
Safety assessments were performed before each treatment. Assessments of total tumor burden via measurements of serum biomarkers were performed at the start of each cycle. Radiologic assessments were made at 12 weeks and every 8 weeks thereafter. Further details concerning the clinical protocol are provided in the Example 3.
Analysis of Mismatch Repair Status
Tumors with genetic defects in MMR pathways are known to harbor thousands of somatic mutations, especially in regions of repetitive DNA known as microsatellites. The accumulation of mutations in these regions of the genome is termed microsatellite instability (MSI) [26-28.] MMR-status was assessed using the MSI Analysis System from Promega in tumors, through the evaluation of selected microsatellite sequences particularly prone to copying errors when MMR is compromised[26-28]. See Supplementary Appendix for additional details.

Genomic & Bioinformatic Analyses

Primary tumor samples and matched normal peripheral-blood specimens were obtained from a subset of subjects with MMR-deficient and others with MMR-proficient carcinomas where sufficient tumor tissue was available for exome sequencing[30] and HLA haplotyping. To assess the potential for mutant peptide binding, somatic exome data combined with the individual patient's MEW class I HLA haplotype was applied to the an epitope prediction algorithm[31, 32]. This algorithm provided an estimate of the total number of mutation-associated neoantigens in each tumor. Additional details are provided in the Supplementary Appendix (available on line at New England Journal of Medicine; incorporated by reference herein).

Statistical Analysis

The primary endpoints for Cohorts A and B were immune-related objective response rate (irORR) and immune-related progression-free survival (irPFS) rate at 20 weeks assessed using immune-related response criteria (irRC)[33].The primary endpoint for Cohort C was irPFS rate at 20 weeks. Immune-related criteria (i.e, criteria used to evaluate immune-based therapies) are based on radiographic responses, and unlike RECIST criteria, capture extent of disease after disease progression; these criteria are defined and compared to RECIST v1.1 in FIG. 10 (Table 51). Response rate and PFS rate at 20 weeks were evaluated and reported in this study using RECIST v1.1 and irRC (FIG. 10 (Table S1)). PFS and overall survival was summarized by Kaplan-Meier method. Details of the hypothesis, the decision rules to reject the null hypotheses and early-stopping rules for efficacy and futility, and statistical methods are provided in the Supplementary Appendix.

EXAMPLE 3

Supplementary Methods

Patients

To be eligible for participation in this study, patients had to be at least 18 years of age, have histologically confirmed evidence of previously-treated, progressive carcinoma. All patients underwent MMR status testing prior to enrollment. All patients had at least one measurable lesion as defined by the Response Evaluation Criteria in Solid Tumors (RECIST), version 1.1, an Eastern Cooperative Oncology Group (ECOG) performance-status score of 0 or 1, and adequate hematologic, hepatic, and renal function. Eligible patients with CRC must have received at least 2 prior cancer therapies and patients with other cancer types must have received at least 1 prior cancer therapy. Patients with untreated brain metastases, history of HIV, hepatitis B, hepatitis C, clinically significant ascites/effusions, or autoimmune disease were excluded.

Study Oversight

Initial drafts of the manuscript were prepared by a subset of the authors and all authors contributed to the final manuscript. All the authors made the decision to submit the manuscript for publication. The principal investigator and study sponsor vouch for the accuracy and completeness of the data reported as well as adherence to the protocol.

HLA Typing

HLA-A, HLA-B and HLA-C Sequence Based Typing can be divided into three distinct steps, as described below. A generic, A*02 specific, B generic, B group specific, C generic and C*07 specific PCR and sequencing mixes were made in the JHU core facility. Celera's AlleleSEQR HLA-B Sequence Based Typing kit was used for B generic SBT. The HLA-A typing scheme is composed of two PCR reactions, A generic and A*02 specific. A generic amplicon encompasses partial exon 1- partial exon 5. A*02 amplicon encompasses partial intron 1—partial exon 5. HLA-B typing scheme is composed of two PCR reactions, B generic and B group specific. The B generic PCR is a multiplexed reaction containing two PCR amplicons encompassing exon 2—exon 3 and exon 4—exon 7. B group specific amplicon encompasses partial intron 1—partial exon 5. HLA-C typing scheme is composed of two PCR reactions, C generic and C*07 specific. C generic and C*07 specific amplicons encompasses exons 1 - 7.

The specificity of the HLA-A and B PCR employed AmpliTaq Gold DNA polymerase. The GeneAmp High Fidelity enzyme is used for the HLA-C and C*07 PCR mixes. This enzyme is a mix of two polymerases: AmpliTaq DNA polymerase (non-proofreading polymerase) and a proofreading polymerase. This enzyme mix is necessary to produce efficient and robust amplification of the larger full length HLA-C amplicon.

PCR product purification was performed using Exonuclease I and Shrimp Alkaline Phosphatase The A generic and B generic amplicons were bi-directionally sequenced for exons 2,3,4. The C generic amplicon was bi-directionally sequenced for exons 2,3 and sequenced in a single direction for exons 1,4,5,6,7. A*02 specific, B group specific and C*07 specific amplicons were sequenced in a single direction for exons 2,3. All sequencing reactions were performed with Big Dye Terminator V1.1 from Applied Biosystems and sequenced with an ABI Prism 3500XL Genetic Analyzer. Conexio Genomic's "Assign SBT" allele assignment software was used to process the data files.

Mismatch Repair Status Testing[1,2]

Six slides of tumor and normal (uninvolved lymph node or margin of resection) were cut (5 microns each), deparaffinized (xylene), and one stained with hematoxylin and eosin (H+E). A tumor area containing at least 20% neoplastic cells, designated by a board-certified Anatomic Pathologist was macrodissected using the Pinpoint DNA isolation system (Zymo Research, Irvine, Calif.), digested in proteinase K for 8 hours and DNA was isolated using a QlAamp DNA Mini Kit (Qiagen, Valencia, CA). MSI was assessed using the MSI Analysis System (Promega, Madison, Wis.), composed of 5 pseudomonomorphic mononucleotide repeats (BAT-25, BAT-26, NR-21, NR-24 and MONO-27) to detect MSI and 2-pentanucleotide repeat loci (PentaC and PentaD) to confirm identity between normal and tumor samples, per manufacturer's instructions. Following amplification of 50-100 ng DNA, the fluorescent PCR products were sized on an Applied Biosystems 3130x1 capillary electrophoresis instrument (Invitrogen, Calsbad, Calif.). Pentanucleotide loci confirmed identity in all cases. Controls included water as a negative control and a mixture of 80% germline DNA with 20% MSI cancer DNA as a positive control. The size in bases was determined for each microsatellite locus and tumors were designated as MSI if two or more mononucleotide loci varied in length compared to the germline DNA.

Sequencing Analysis

Samples

Samples provided as FFPE blocks or frozen tissue underwent pathological review to determine tumor cellularity. Tumors were macrodissected to remove contaminating normal tissue, resulting in samples containing >20% neoplastic cells. Matched normal samples were provided as blood, saliva or normal tissue obtained from surgery.

Sample Preparation and Next-Generation Sequencing[3]

Sample preparation, library construction, exome capture, next generation sequencing, and bioinformatics analyses of tumor and normal samples were performed at Personal Genome Diagnostics, Inc. (Baltimore, Maryland). In brief, DNA was extracted from frozen or formalin-fixed paraffin embedded (FFPE) tissue, along with matched blood or saliva samples using the Qiagen DNA FFPE tissue kit or Qiagen DNA blood mini kit (Qiagen, Calif.). Genomic DNA from tumor and normal samples were fragmented and used for Illumina TruSeq library construction (Illumina, San Diego, Calif.) according to the manufacturer's instructions or as previously described4. Briefly, 50 nanograms (ng)—3 micrograms (μg) of genomic DNA in 100 microliters (μl) of TE was fragmented in a Covaris sonicator (Covaris, Woburn, Mass.) to a size of 150-450bp. To remove fragments smaller than 150bp, DNA was purified using Agencourt AMPure XP beads (Beckman Coulter, Ind.) in a ratio of 1.0 to 0.9 of PCR product to beads twice and washed using 70% ethanol per the manufacturer's instructions. Purified, fragmented DNA was mixed with 36 μl of H2O, 10 μl of End Repair Reaction Buffer, 5 μl of End Repair Enzyme Mix (cat# E6050, NEB, Ipswich, Mass.). The 100 μl end-repair mixture was incubated at 20° C. for 30 min, and purified using Agencourt AMPure XP beads (Beckman Coulter, Ind.) in a ratio of 1.0 to 1.25 of PCR product to beads and washed using 70% ethanol per the manufacturer's instructions. To A-tail, 42 μl of end-repaired DNA was mixed with 5μl of 10X dA Tailing Reaction Buffer and 3 μl of Klenow (exo-)(cat# E6053, NEB, Ipswich, Mass.). The 50 μl mixture was incubated at 37° C. for 30 min and purified using Agencourt AMPure XP beads (Beckman Coulter, Ind.) in a ratio of 1.0 to 1.0 of PCR product to beads and washed using 70% ethanol per the manufacturer's instructions. For adaptor ligation, 25 μl of A-tailed DNA was mixed with 6.7 μl of H2O, 3.3 μl of PE-adaptor (Illumina), 10 μl of 5X Ligation buffer and 5 μl of Quick T4 DNA ligase (cat# E6056, NEB, Ipswich, Mass.). The ligation mixture was incubated at 20° C. for 15 min and purified using Agencourt AMPure XP beads (Beckman Coulter, Ind.) in a ratio of 1.0 to 0.95 and 1.0 of PCR product to beads twice and washed using 70% ethanol per the manufacturer's instructions. To obtain an amplified library, twelve PCRs of 25 μl each were set up, each including 15.5 μl of H2O, 5 μl of 5× Phusion HF buffer, 0.5 μl of a dNTP mix containing 10 mM of each dNTP, 1.25 μl of DMSO, 0.25 μl of Illumina PE primer #1, 0.25 μl of Illumina PE primer #2, 0.25 μl of Hotstart Phusion polymerase, and 2 μl of the DNA. The PCR program used was: 98° C. for 2 minutes; 12 cycles of 98° C. for 15 seconds, 65° C. for 30 seconds, 72° C. for 30 seconds; and 72° C. for 5 min. DNA was purified using Agencourt AMPure XP beads (Beckman Coulter, IN) in a ratio of 1.0 to 1.0 of PCR product to beads and washed using 70% ethanol per the manufacturer's instructions. Exonic or targeted regions were captured in solution using the Agilent SureSelect v.4 kit according to the manufacturer's instructions (Agilent, Santa Clara, Calif.). The captured library was then purified with a Qiagen MinElute column purification kit and eluted in 17 μl of 70° C. EB to obtain 15 μl of captured DNA library. (5) The captured DNA library was amplified in the following way: Eight 30 uL PCR reactions each containing 19 μl of H2O, 6 μl of 5× Phusion HF buffer, 0.6 μl of 10 mM dNTP, 1.5 μl of DMSO, 0.30 μl of Illumina PE primer #1, 0.30 μl of Illumina PE primer #2, 0.30 μl of Hotstart Phusion polymerase, and 2 μl of captured exome library were set up. The PCR program used was: 98° C. for 30 seconds; 14 cycles (exome) or 16 cycles (targeted) of 98° C. for 10 seconds, 65° C. for 30 seconds, 72° C. for 30 seconds; and 72° C. for 5 min. To purify PCR products, a NucleoSpin Extract II purification kit (Macherey-Nagel, Pa.) was used following the manufacturer's instructions. Paired-end sequencing, resulting in 100 bases from each end of the fragments for exome libraries and 150 bases from each end of the fragment for targeted libraries, was performed using Illumina HiSeq 2000/2500 and Illumina MiSeq instrumentation (Illumina, San Diego, Calif.).

Primary Processing of Next-Generation Sequencing Data and Identification of Putative Somatic Mutations3

Somatic mutations were identified using VariantDx custom software (Personal Genome Diagnostics, Baltimore, Maryland) for identifying mutations in matched tumor and normal samples. Prior to mutation calling, primary processing of sequence data for both tumor and normal samples were performed using Illumina CASAVA software (v1.8), including masking of adapter sequences. Sequence reads were aligned against the human reference genome (version hg18) using ELAND with additional realignment of select regions using the Needleman-Wunsch method 5. Candidate somatic mutations, consisting of point mutations, insertions, and deletions were then identified using VariantDx across the either the whole exome or regions of interest. VariantDx examines sequence alignments of tumor samples against a matched normal while applying filters to exclude alignment and sequencing artifacts. In brief, an alignment filter was applied to exclude quality failed reads, unpaired reads, and poorly mapped reads in the tumor. A base quality filter was applied to limit inclusion of bases with reported phred quality score >30 for the tumor and >20 for the normal. A mutation in the tumor was identified as a candidate somatic mutation only when (i) distinct paired reads contained the mutation in the tumor; (ii) the number of distinct paired reads containing a particular mutation in the tumor was at least 10% of read pairs; (iii) the mismatched base was not present in >1% of the reads in the matched normal sample as well as not present in a custom database of common germline variants derived from dbSNP; and (iv) the position was covered in both the tumor and normal at >150X. Mutations arising from misplaced genome alignments, including paralogous sequences, were identified and excluded by searching the reference genome.

Candidate somatic mutations were further filtered based on gene annotation to identify those occurring in protein-coding regions. Functional consequences were predicted using snpEff and a custom database of CCDS, RefSeq and Ensembl annotations using the latest transcript versions available on hg18 from UCSC (available at genome.us-c.edu). Predictions were ordered to prefer transcripts with canonical start and stop codons and CCDS or Refseq transcripts over Ensembl when available. Finally mutations were filtered to exclude intronic and silent changes, while retaining mutations resulting in missense mutations, nonsense mutations, frameshifts, or splice site alterations. A manual visual inspection step was used to further remove artifactual changes.

Mutant Peptide MHC Binding Prediction

Somatic frameshift, insertions, deletions, and missense mutations predicted to result in an amino acid change were analyzed for potential MHC class I binding based on the individual patient's HLA haplotype. Our initial analysis focused on HLA-A and HLA-B. Amino acid mutations were linked to their corresponding CCDS accession number and in instances where this was unavailable, either a Refseq or ensemble transcript was used to extract the protein sequence. To identify 8mer, 9mer, and 10mer epitopes, amino acid fragments surrounding each mutation were identified. These 15, 17, and 19 mutant amino acid fragments were analyzed by the epitope prediction program NetMHC 3.4.6 Epitopes with a predicted affinity of <50nm were considered to be strong potential binders and epitopes with a predicted affinity of <500nm were considered to be weak potential binders as suggested by the NetMHC group6.

To further refine the total neoantigen burden, we repeated that same process for the complementary wild-type peptide for each mutant peptide. We then filtered for mutant peptides that were strong potential binders when the complementary wild-type peptide was predicted a weak potential binder. These mutant peptides are referred to as mutation-associated neoantigens (MANA). In the event that a patient had a (e.g., cases 1, 17 and 21) single MHC haplotype not supported by NetMHC 3.4, the individual haplotype was not included in our analysis.

Statistical Methods

Design of the Trial[7]

This trial was conducted using a parallel two-stage design to simultaneously evaluate the efficacy of MK-3475 and MSI as a treatment selection marker for anti-PD-1 therapy. It consisted of two-stage phase 2 studies in parallel in the three cohorts of patients described in the text. The study agent, MK-3475, was administered at 10 mg/kg intravenously every 14 days.

For each of Cohort A and B, the co-primary endpoints were progression-free-survival (irPFS) at 20 weeks and objective response (irOR) assessed using immune related criteria. A step-down gatekeeping procedure was used to preserve the overall type I error. A two-stage Green-Dahlberg design was used to evaluate irPFS, with interim and final analysis after 15 and 25 patients, respectively. At stage 1, ≥1 of 15 free-of-progression at 20 weeks were required to proceed to the second stage, and ≥4 of 25 free-of-progression at 20 weeks were then required to proceed to test for irOR, with ≥4 of 25 responders (irCR or irPR) indicating promising efficacy in that cohort. Each cohort could be terminated for efficacy as soon as ≥4 free-of-progression at 20 weeks and ≥4 responses were confirmed, or be terminated for futility as soon as 0 of 15 in stage 1 were free-of-progression at 20 weeks or ≥22 subjects had disease progression by 20 weeks. This design achieves 90% power to detect a 20-week irPFS rate of 25% and 80% power to detect an irOR rate (irORR) of 21%, with an overall type I error of 0.05 at the null hypothesis of 20-week irPFS rate of 5% and irORR of 5%.

For Cohort C, the primary endpoint was irPFS at 20 weeks. A two-stage Green-Dahlberg two-stage design was used, with an interim and final analysis after 14 and 21 patients; at stage 1, ≥1 of 14 free-of-progression at 20 weeks were required to proceed to the second stage, with ≥4 of 21 free-of-progression at 20 weeks at the end indicating adequate efficacy in Cohort C. The cohort could be terminated as soon as ≥4 free-of-progression at 20 weeks were confirmed. The design has 81% power to detect a 20-week irPFS rate of 25% with a 5% type I error at the null hypothesis of 20-week irPFS rate of 5%.

Statistical Analysis

Response and progression were evaluated using RECIST v1.1 and the immune-related response criteria (irRC) adopted from Wolchok et al.8, which uses the sum of the products of bidimensional tumor measurements and incorporates new lesions into the sum. Progression-free survival (PFS) rates and irPFS rate at 20-weeks was estimated as the proportion of patients who were free-of-disease progression and alive at 20 weeks after the initiation of pembrolizumab. Patients who had disease progression prior to 20 weeks or were enrolled for >20 weeks at the time the study data were collated were included in the analysis for estimating 20-week PFS (irPFS) rate. Patients who dropped out early due to toxicities or worsening disease and therefore did not have 20-week tumor assessment were considered as having progressive disease. ORR (irORR) was the proportion of patients who achieved best overall response of CR or PR (irCR or irPR). Patients who were in the study long enough to have tumor response evaluations were included in the analysis for estimating response rates. Among those who responded (CR or PR), duration of response was the time of first RECIST response to the time of disease progression, and was censored at the last evaluable tumor assessment for responders who had not progressed.

PFS and irPFS were defined as the time from the date of initial dose to the date of disease progression or the date of death due to any cause, whichever occurred first. PFS and irPFS were censored on the date of the last evaluable tumor assessment documenting absence of progressive disease for patients who were alive and progression-free. Overall survival (OS) was defined as the time from the date of initial dose to death due to any cause. For patients who were still alive at the time of analysis, the OS time was censored on the last date the patients were known to be alive. Survival times were summarized by the Kaplan-Meier method. As a post hoc analysis, log-rank tests were used to compare Cohort A and B and hazard ratios were estimated based on Cox models.

The association of percent CEA decline after 1 cycle with PFS or OS was assessed using landmark analysis based on Cox regression models. For correlative studies, non-parametric Wilcoxon test was used to compare mutational load between MMR-deficient and MMR-proficient patients. The effects of baseline mutational burden and immune markers on response and survival times were examined using logistic regression and Cox regression, respectively.

Immunohistochemistry & Image Analysis

The fraction of malignant cells exhibiting a membranous pattern of B7-H1 expression and the percentage at the invasive front were quantified by three pathologists (R.A.A., F.B., and J.M.T.) as previously reported9,10. Image analysis was used to determine the number of CD8 diaminobenzidine (DAB)-stained cells. Using the H&E-stained slide for each case, we identified the following regions: i) tumor, ii) invasive front (the boundary between malignant and non-malignant tissue), and iii) normal tissue. The CD8-stained slides were scanned at 20× equivalent magnification (0.49 micrometers per pixel) on an Aperio ScanScope AT. Regions corresponding to tumor, invasive front and normal tissue (above, from the H&E) were annotated on separate layers using Aperio ImageScope v12.1.0.5029.

CD8-positive lymphocyte density was calculated in each of the above regions using a custom algorithm implemented in PIP11. Results were converted to Deepzoom images using the VIPS library12 and visualized using the OpenSeadragon viewer (available at openseadragon.github.io).

REFERENCES FOR EXAMPLE 3 ONLY

1. Bacher J W, Flanagan L A, Smalley R L, et al. Development of a fluorescent multiplex assay for detection of MSI-High tumors. Disease markers 2004;20:237-50.
2. Murphy K M, Zhang S, Geiger T, et al. Comparison of the microsatellite instability analysis system and the Bethesda panel for the determination of microsatellite instability in colorectal cancers. The Journal of molecular diagnostics : JMD 2006;8:305-11.
3. Jones S, Anagnostou V, Lytle K, et al. Personalized genomic analyses for cancer mutation discovery and interpretation. Science translational medicine 2015;7: 283ra53.
4. Sausen M, Leary R J, Jones S, et al. Integrated genomic analyses identify ARID1A and ARID1B alterations in the childhood cancer neuroblastoma. Nature genetics 2013; 45:12-7.
5. Needleman S B, Wunsch C D. A general method applicable to the search for similarities in the amino acid sequence of two proteins. Journal of molecular biology 1970;48:443-53.
6. Lundegaard C, Lamberth K, Harndahl M, Buus S, Lund O, Nielsen M. NetMHC-3.0: accurate web accessible predictions of human, mouse and monkey MHC class I affinities for peptides of length 8-11. Nucleic acids research 2008;36:W509-12.
7. Buyse M, Michiels S, Sargent D J, Grothey A, Matheson A, de Gramont A. Integrating biomarkers in clinical trials. Expert review of molecular diagnostics 2011;11:171-82.
8. Wolchok J D, Hoos A, O'Day S, et al. Guidelines for the evaluation of immune therapy activity in solid tumors: immune-related response criteria. Clinical cancer research : an official journal of the American Association for Cancer Research 2009;15:7412-20.
9. Llosa N J, Cruise M, Tam A, et al. The vigorous immune microenvironment of microsatellite instable colon cancer is balanced by multiple counter-inhibitory checkpoints. Cancer Discov 2015:43-51.
10. Taube J M, Anders R A, Young G D, et al. Colocalization of Inflammatory Response with B7-H1 Expression in Human Melanocytic Lesions Supports an Adaptive Resistance Mechanism of Immune Escape. Science Translational Medicine 2012;4:127ra37.
11. Cuka N, Hempel H, Sfanos K, De Marzo A, Cornish T. PIP: An Open Source Framework for Multithreaded Image Analysis of Whole Slide Images. LABORATORY INVESTIGATION 2014;94:398A-A.
12. Cupitt J, Martinez K. VIPS: an image processing system for large images. Electronic Imaging: Science & Technology; 1996: International Society for Optics and Photonics. p. 19-28.

EXAMPLE 4

Patients 41 consecutive patients were enrolled and treated between September 2013 and January 2015. (Table 1). Recruitment included patients in pursuit of a clinical trial option who were known to have tumors with mismatch repair, or who had tumors of unknown status who were then tested. One patient in the MMR-deficient CRC cohort was enrolled under an IRB eligibility waiver allowing a grade 3 bilirubin level. A total of 32 CRC patients were enrolled into Cohorts A and B. All CRC patients received ≥2 prior chemotherapy regimens (median=4) except for one MMR-proficient patient who had received one chemotherapeutic and one (non-PD1-based) immunotherapeutic regimen.

Nine subjects diagnosed with MMR-deficient solid tumors other than CRC were enrolled onto Cohort C. All Cohort C patients received ≥1 prior cancer treatments (median=2).

EXAMPLE 5

Primary Endpoint Evaluation

The irORR and irPFS at 20 weeks (FIG. 11 (Table S2)) for Cohort A were 40% (4 of 10 patients; 95% CI, 12 to 74%) and 78% (7 of 9 patients; 95% CI, 40 to 97%) and for Cohort C were 71% (5 of 7 patients; 95% CI, 29 to 96%) and 67% (4 of 6 patients; 95% CI, 22 to 96%). In Cohort B, comprised of patients with MMR-proficient CRCs, irORR and 20-week irPFS were 0% (95% CI, 0 to 20%) and 11% (2 of 18 patients; 95% CI, 1 to 35%). Both the MMR-deficient cohorts A and C reached their predefined early stopping rule for efficacy when four subjects were free-of-disease progression at 20 weeks and four objective responses were observed based on immune-related response criteria (FIG. 11 (Table S2); available on line at New England Journal of Medicine; incorporated by reference herein; and supplementary methods, above).

The median time of follow-up for patients was 32 weeks (range, 5-51 weeks) for patients with MMR-deficient CRC (Cohort A), 12 weeks (range, 2-56 weeks) for patients with MMR-proficient CRC (Cohort B) and 12 weeks (range, 4-42 weeks) for patients with MMR-deficient non-CRC tumors (Cohort C). All patients evaluable for 20-week irPFS were followed for at least 20 weeks.

EXAMPLE 6

Radiographic Evaluation

Figure 3:
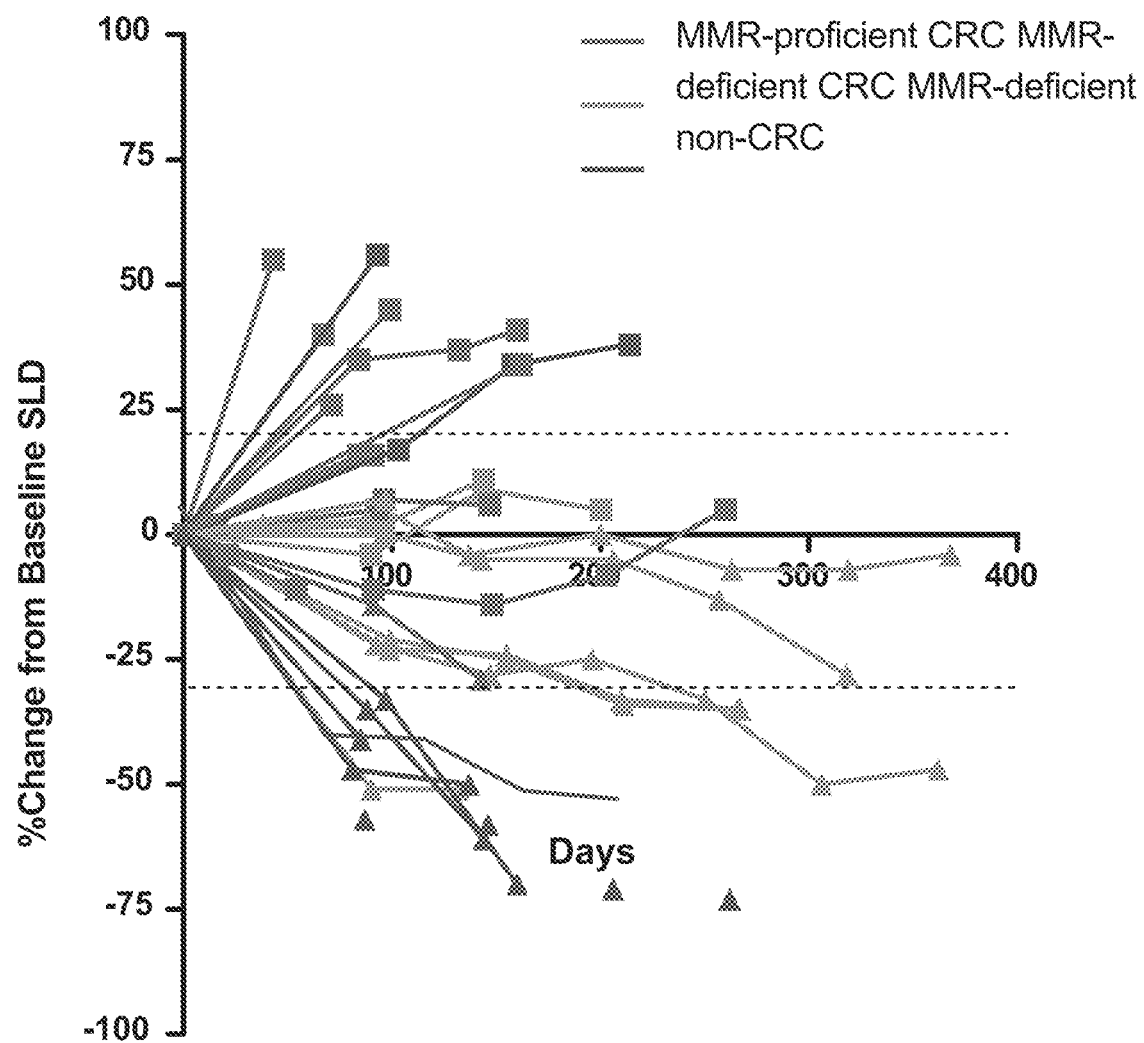
FIG. 3 (FIG. S2) Spider plot of radiographic response. Tumor responses were measured at regular intervals and values show percent change of the sum of longest diameters (SLD) from the baseline measurements of each measurable tumor. Patients were only included if baseline and on study treatment scans were available. Green and red represent patients with MMR-deficient and proficient CRCs, respectively. Blue represents patients with MMR-deficient cancers other than CRC.

Of the ten evaluable MMR-deficient CRC patients in Cohort A, four (40%; 95% CI, 12-74%) achieved objective responses by RECIST criteria (Table 2, FIG. 1 and FIG. 3 (S2)). Patients were considered not evaluable unless they underwent a 12-week scan. The disease control rate was defined as the fraction of patients who achieved an objective response or whose disease was stable, and was 90% in Cohort A (9 of 10 patients; 95% CI, 55-100%).

Of the seven evaluable patients with MMR-deficient cancer types other than CRC enrolled in Cohort C, five (71%; 95% CI, 29-96%) achieved objective responses (Table 2, FIG. 3 (S2) and FIG. 1) using RECIST criteria and the disease control rate was 71% (5 of 7 patients; 95% CI, 29-96%).

Patients in Cohort C responded faster than patients in Cohort A (median time to response by RECIST of 12 vs. 28 weeks, p=0.03). Furthermore, all six MMR-deficient tumors that were not associated with Lynch syndrome (100%) achieved an objective response, whereas only three of eleven tumors (27%) associated with Lynch Syndrome responded (Table S3; p=0.009; available on-line at New England Journal of Medicine; and incorporated by reference herein). No other baseline characteristics showed statistically significant association with objective responses.

Of the 18 patients with MMR-proficient CRCs in Cohort B, no objective responses were observed (Table 2, FIG. 3 (S2) and FIG. 1) using RECIST criteria and the disease control rate was 11% (2 of 18 patients; 95%CI, 1 to 35%).

All patients who achieved a response by RECIST criteria (FIG. 11 (Table 2)) also achieved a response by immune-related response criteria (FIG. 11 (Table S2)).

EXAMPLE 7

Survival

Figures 2A, 2B, 2C, 2D:
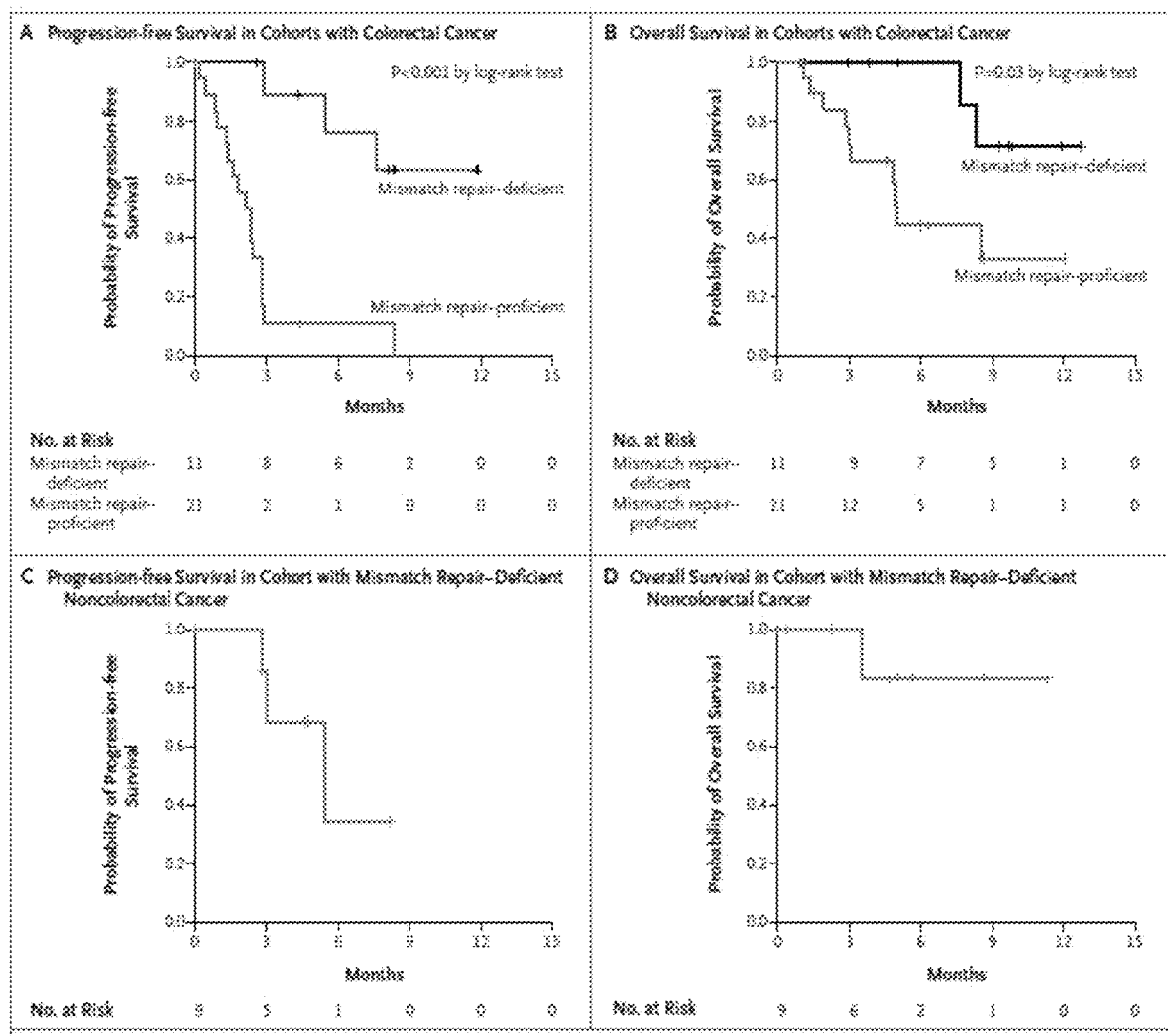
FIGS. 2A-2D. Clinical benefit to pembrolizumab according to MMR status. Kaplan-Meier curves are shown for (FIG. 2A) progression-free survival in the colorectal cancer cohorts, (FIG. 2B) overall survival in the colorectal cancer cohorts, (FIG. 2C) progression-free survival of patients with MMR-deficient cancers other than colorectal (median PFS=5.4 months; 95% CI, 3% to not estimable), and (FIG. 2D) overall survival of patients with MMR-deficient cancers other than colorectal. In both cohorts with MMR-deficient tumors (CRC and non-CRC), median overall survival was not reached. Patients in the cohort with MMR-proficient cancers had a median PFS of 2.2 months (95% CI 1.4 to 2.8%) and a median OS of 5.0 months (95% CI 3.0 to not estimable).

In Cohort A, the patients with MMR-deficient CRC, median progression-free survival (PFS) and median overall survival (OS) were not reached (FIG. 2). In contrast, the patients with MMR-proficient cancers in Cohort B achieved a PFS of only 2.2 months (95% CI, 1.4-2.8) and a median OS of 5.0 months (95% CI, 3.0 to not estimable). In Cohort C (MMR-deficient non-CRC), the median PFS was 5.4 months (95% CI, 3 to not estimable) and the median OS was not reached.

A post hoc (FIG. 2) comparison of the MMR-deficient and proficient CRC cohorts showed hazard ratios (HR) for disease progression (HR=0.10; 95% CI, 0.03-0.37; p<0.001) and overall survival (HR=0.22; 95% CI, 0.05-1.00; p=0.05), favoring patients with MMR-deficient CRC.

Figure 4A:
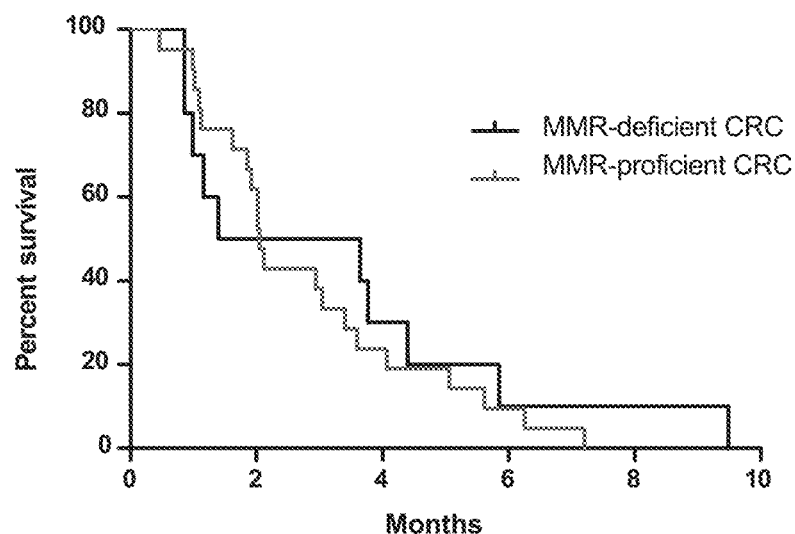
FIGS. 4A-4B (FIG. S3). MMR-proficient and deficient CRCs have comparable time on treatment and duration of metastatic disease prior to study enrollment. Kaplan-Meier estimates of (FIG. 4A) time on therapy immediately prior to study enrollment (HR 0.81, 95% CI 0.38 to 1.752, p=.60) and (FIG. 4B) duration of metastatic disease prior to enrollment (HR 1.13, 95% CI 0.49 to 2.62, p=.'78) on this pembrolizumab study were comparable between the MMR-deficient and proficient CRC cohorts. The short duration on prior therapy is expected in a treatment refractory CRC population.
Figure 4B:
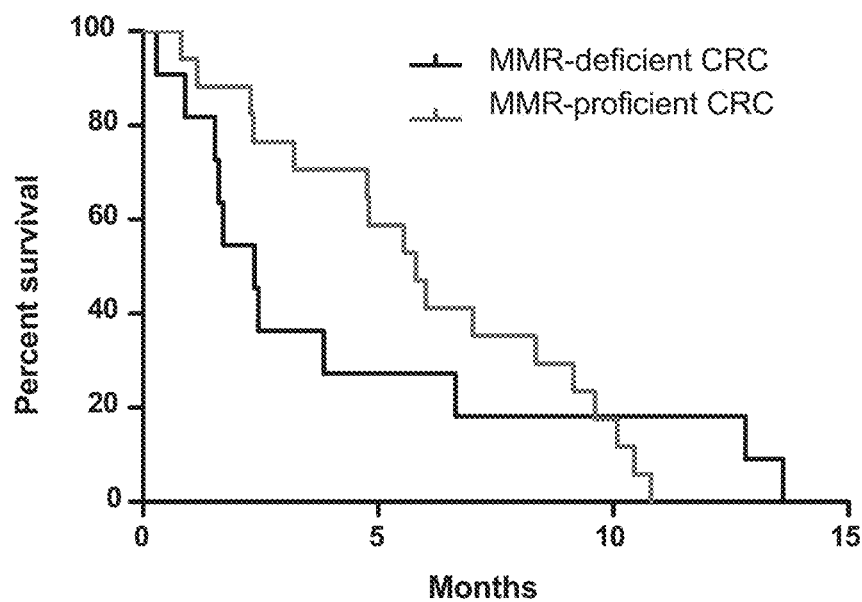

To evaluate whether the difference in survival might be due to prognostic differences, we measured the duration of time patients had been diagnosed with metastatic disease and the clinical performance of patients on their previous regimen prior to enrollment. We found that there was no significant difference between MMR-deficient vs. MMR-proficient CRC patients with respect to their duration of metastatic disease (p=0.77; Log-rank test) or median PFS (p=0.60, Log-rank test) on their prior regimens (FIG. 4 (S3)). We also performed an additional multivariate analysis of PFS and OS to examine the difference in outcomes between MMR-deficient CRC and MMR-proficient tumors adjusting for elapsed time since initial diagnosis. The magnitude of the hazard ratios for PFS (HR 0.04, 95% CI 0.01-0.21, P<0.001) and OS (HR 0.18, 95% CI 0.03-1.01, P=0.05), representing the different effect of pembrolizumab between MMR-deficient and MMR-proficient tumors, was maintained after adjusting for this potential difference.

EXAMPLE 8

Safety Assessment

Adverse events occurring in >5% of patients are listed in Table 3. Select adverse events included rash/pruritus (24%), thyroiditis/hypothyroidism/hypophysitis (10%), and asymptomatic pancreatitis (15%). While the numbers were small, thyroid function abnormalities were limited to the MMR-deficient cohorts (Table 3).

EXAMPLE 9

Tumor Markers

Figure 5:
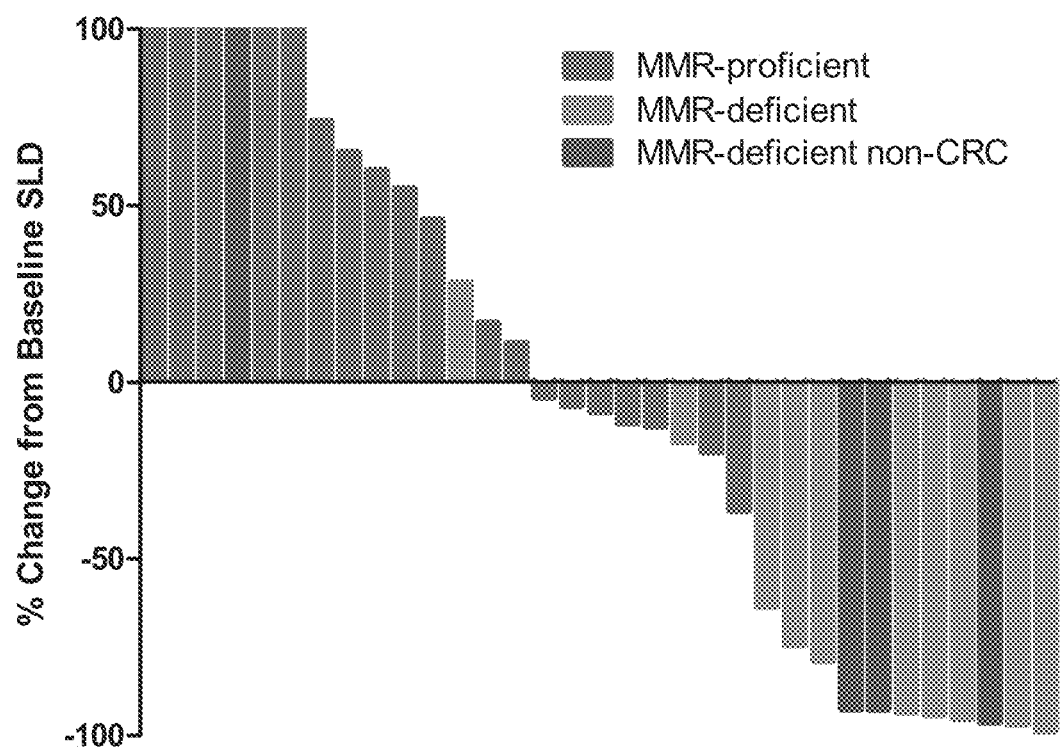
FIG. 5 (FIG. S4.) Waterfall plot of biochemical response. Serum protein biomarker levels were measured with each cycle and the values represent best percent change from baseline. Patients were included if baseline tumor marker values were greater than the upper limit of normal. CA-125 was used for a patient with endometrial cancer; CA19-9 was used for 1 cholangiocarcinoma and 1 ampullary cancer; and CEA was used for all other patients. Green and red represent patients with MMR-deficient and proficient CRCs, respectively. Blue represents patients with MMR-deficient cancers other than CRC.

In the two CRC cohorts, baseline CEA levels were evaluable and above the upper limit of normal (3 mg/dl), in 29 of 32 patients prior to enrollment. Major CEA declines occurred in seven of the ten patients with MMR-deficient CRC and in none of the 19 patients with MMR-proficient CRCin which CEA was evaluable (FIG. 1 and FIG. 5 (S4)). In non-CRC MMR-deficient patients, tumor marker levels (CEA, CA19-9 or CA-125) were elevated above the upper limit of normal in four patients. CA19-9 or CA-125 declines of >70% occurred in three of these four patients. Tumor marker kinetics of all 3 cohorts are shown in FIG. 1. The level of CEA decline after 1 dose (between days 14 and 28) of pembrolizumab was predictive of both progression-free (p=0.01) and overall survival outcomes (p=0.02). The CEA response occurred well in advance of radiographic confirmation of disease control (range, 10 to 35 weeks). In contrast, patients who progressed showed rapid biomarker elevation within 30 days of initiating therapy. Thus, changes in CEA levels significantly preceded and correlated with ultimate radiographic changes.

EXAMPLE 10

Genomic Analysis

Analysis of whole-exome sequences showed an average of 1,782 somatic mutations per tumor in MMR-deficient patients (n =9) compared with 73 mutations per tumor in MMR-proficient patients (n=6) (non-parametric Wilcoxon test, p=0.007) (FIGS. 6A-6B (S5); see also Table S3 which is available on-line at New England Journal of Medicine; incorporated by reference herein). Most (63%) of these mutations are predicted to alter amino acids.

These mutations were then assessed for their immunogenic potential in the context of each patient's individual MHC haplotype. We thereby identified an average of 578 and 21 potential mutation-associated neoantigens from the tumors of MMR-deficient and MMR-proficient patients, respectively (Table S3; which is available on-line at New England Journal of Medicine; incorporated by reference herein). The fraction of potential mutation-associated neoantigens among all somatic mutations was similar in both cohorts (averaging 32% and 29% in MMR-deficient and -proficient patients, respectively). High numbers of somatic mutations and potential mutation-associated neoantigens were associated with improved progression-free survival and with a trend in favor of objective response (FIG. 13 (S5) and FIG. 12 (Table S4); also available on line at New England Journal of Medicine; incorporated by reference herein).

EXAMPLE 11

Immunohistochemistry

Figure 7:
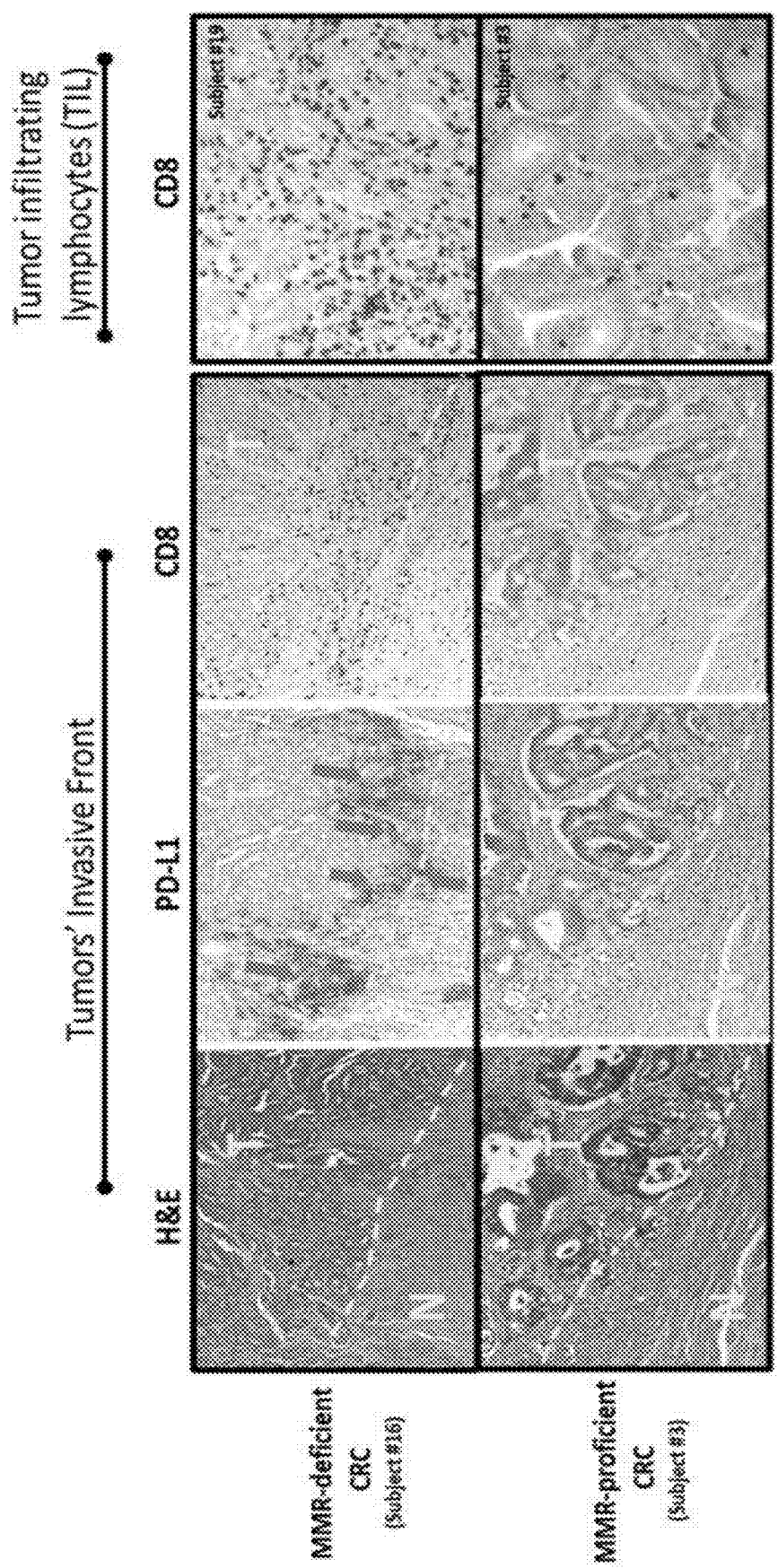
FIG. 7 (FIG. S6). Immunohistochemistry of CD8 and PD-L1 Expression. The invasive front (yellow dashed line) from a MMR-deficient CRC (subject #16, top) and MMR-proficient CRC (subject #3, bottom). The yellow dashed line separates tumor (T) and normal (N) tissue. There is marked expression of PD-L1 (blue arrows) and CD8 (brown dots) in the MMR-deficient tumor (top panels) patient while there is very little expression of either marker in the MMR-proficient tumor (bottom panels). Representative images of tumor infiltrating lymphocytes (TIL) in another MMR-deficient CRC (subject #19, top) and MMR-proficient CRC (subject #3, bottom) immunolabeled with an antibody to CD8(brown dots). Note the infiltration of CD8 cells in the MMR-deficient tumor. Invasive front original magnification 10x and TIL 20x.
Figure 8:
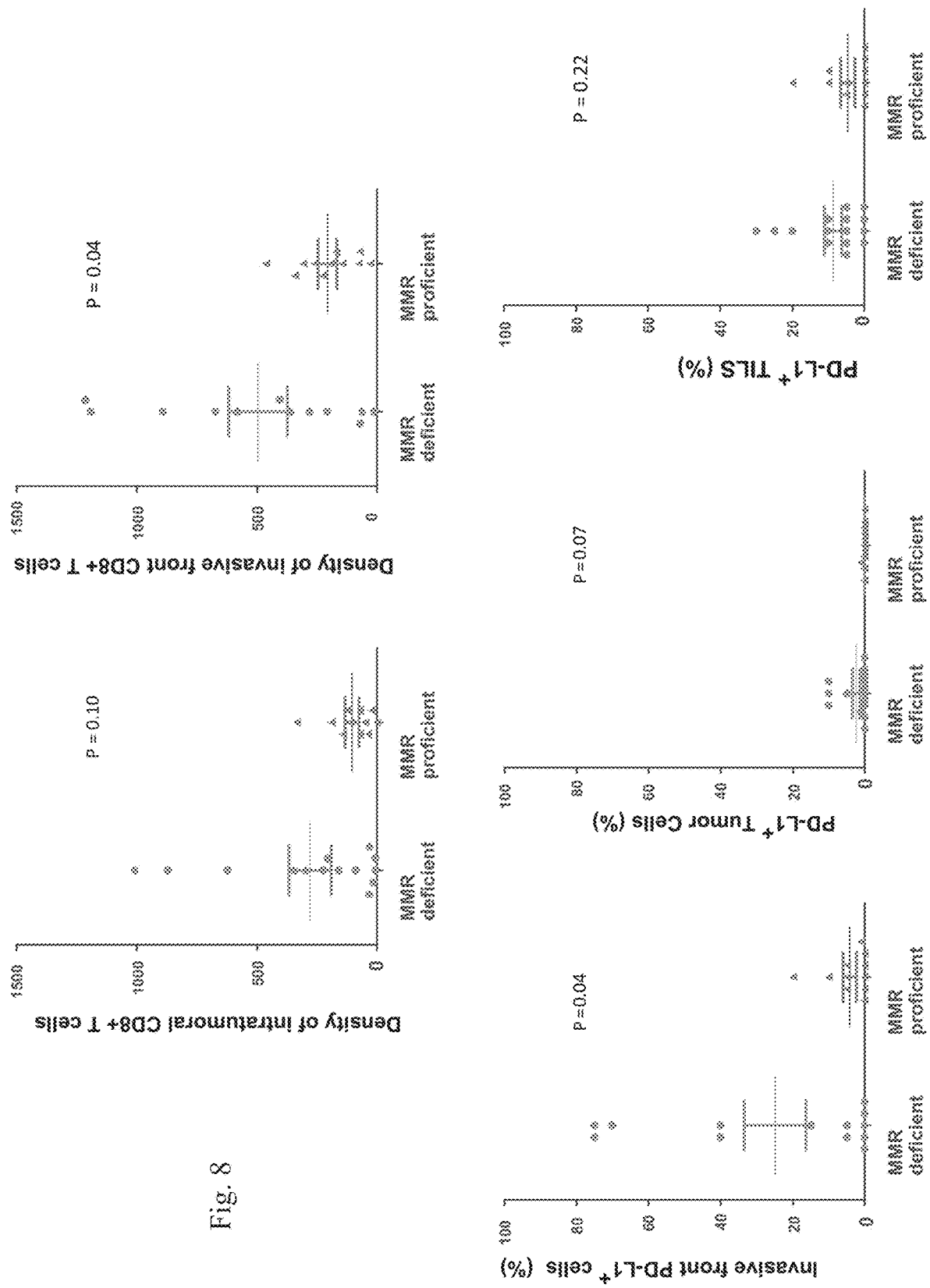
FIG. 8 (FIG. S7.) CD8 and PD-L1 Expression in the MMR-deficient and MMR-proficient tumor microenvironment. T cell density units are cells/mm2 of tumor. Invasive front refers to the immune cells (TILs and macrophages) at the junction of the tumor and normal tissue. P-values obtained using an unpaired t-test.
Figure 9:
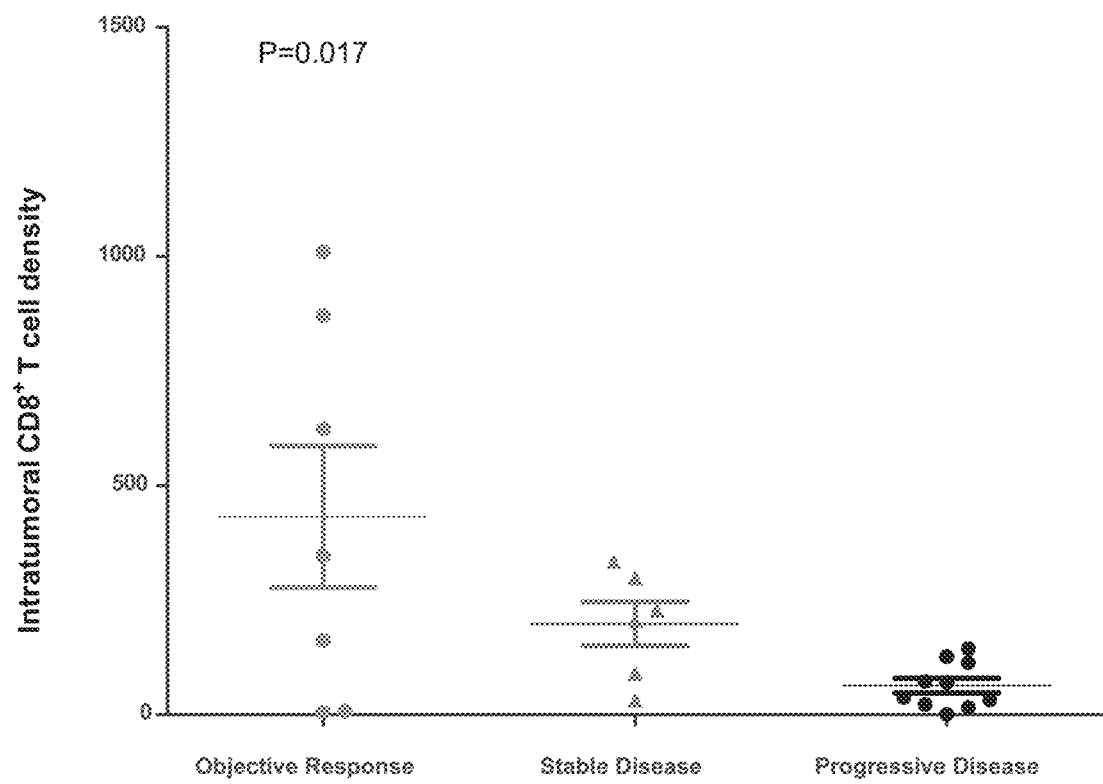
FIG. 9 (FIG. S8.) CD8 expression and clinical benefit to pembrolizumab. Correlation between the intratumoral CD8$^+$ T cell density (cells/mm2) and objective response (Jonckheere-Terpstra test for trend, p=0.02).

Expression of CD8 and PD-L1 were evaluated by immunohistochemistry within the tumor and at the invasive fronts of the tumor in the 30 cases in which tumor tissue was available (FIG. 7 (S6); also available on line at New England Journal of Medicine; incorporated by reference herein). Tumors from patients in Cohorts A and C contained a greater density of CD8-positive lymphoid cells than did tumors from Cohort B patients (FIG. 8 (S7); p=0.10) and CD8-labeling was associated with a trend favoring objective response and stable disease (FIG. 9 (S8) and FIG. 13 (Table S5); also available on line at New England Journal of Medicine; incorporated by reference herein). This CD8-positive lymphoid infiltrate was especially prominent at the invasive fronts of the tumors (FIG. 8 (S7); p=0.04). Significant membranous PD-L1 expression only occurred in MMR-deficient patients and was prominent on tumor infiltrating lymphocytes (TILs) and tumor-associated macrophages located at the tumors' invasive fronts (FIG. 8 (S7); p=0.04). Expression of CD8 and PD-L1 were not statistically associated with PFS or OS (FIG. 13 (Table S5)).

TABLE 1

Demographic and Baseline Characteristics of Patients

| Characteristic | MMR-deficient CRC n = 11 | MRC-proficient CRC n = 21 | P values[1] | MMR-deficient non-CRC n = 9 |
|---|---|---|---|---|
| Age-years | | | | |
| median | 46 | 61 | 0.02 | 57 |
| range | (24-65) | (32-79) | | (34-92) |
| Sex-no. (%) | | | | |
| Female | 5(45) | 8(38) | 0.72 | 4(44) |
| Male | 6(55) | 13(62) | | 5(56) |
| Race-no. (%) | | | | |
| white | 8(73) | 17(81) | 0.66 | 8(89) |
| black | 1(9) | 3(14) | | 0(0) |
| other | 2(18) | 1(5) | | 1(11) |

TABLE 1-continued

Demographic and Baseline Characteristics of Patients

| Characteristic | MMR-deficient CRC n = 11 | MRC-proficient CRC n = 21 | P values[1] | MMR-deficient non-CRC n = 9 |
|---|---|---|---|---|
| ECOG Performance Status-no. (%)[2] | | | | |
| 0 | 0(0) | 6(29) | 0.07 | 2(22) |
| 1 | 11(100) | 15(71) | | 7(78) |
| Diagnosis-no. (%) | | | | |
| Colon | 9(82) | 18(86) | >0.99 | 0(0) |
| Rectal | 2(18) | 3(14) | | 0(0) |
| Ampullary/Cholangiocarcinoma | 0(0) | N/A | | 4(44) |
| Endometrial | 0(0) | N/A | | 2(22) |
| Small bowel | 0(0) | N/A | | 2(22) |
| Gastric | 0(0) | N/A | | 1(11) |
| Histology-no. (%) | | | | |
| Well/moderately differentiated | 7(64) | 18(86) | 0.20 | 4(44) |
| Poorly differentiated | 4(36) | 3(14) | | 3(33) |
| Other | 0(0) | 0(0) | | 2(22) |
| Stage IV-no. (%) | (11)100 | 21(100) | >0.99 | 9(100) |
| Liver metastases-no. (%) | 6(55) | 11(52) | >0.99 | 6(67) |
| Time since first diagnosis-months | | | | |
| median | 31 | 58 | 0.07 | 23 |
| range | 6-95 | 27-192 | | 2-105 |
| Prior systemic therapies-no. (%) | | | | |
| 0 | 0(0) | 0(0) | 0.89 | 1(11) |
| 2 | 3(27) | 4(19) | | 5(56) |
| 3 | 3(27) | 5(24) | | 1(11) |
| >4 | 5(45) | 12(57) | | 2(22) |
| Detected germline mutation or known Lynch-no. (%) | | | | |
| Yes | 9(82) | 0(0) | <0.001 | 4(44) |
| No | 2(18) | 21(100) | | 4(44) |
| Unknown | 0(0) | 0(0) | | 1(11) |
| BRAF wild type-no. (%) | | | | |
| Yes | 8(73) | 11(52) | 0.64 | 4(44) |
| No | 0(0) | 1(5) | | 0(0) |
| Unknown | 3(27) | 9(43) | | 5(56) |
| KRAS wild type-no. (%) | | | | |
| Yes | 6(55) | 13(62) | 0.72 | 4(44) |
| No | 5(45) | 8(38) | | 1(11) |
| Unknown | 0(0) | 0(0) | | 4(44) |

MMR, mismatch repair; CRC, colorectal cancer
[1]MMR-deficient CRC versus MMR-proficient CRC
[2]ECOG, Eastern Cooperative Oncology Group

TABLE 2

Objective RECIST responses

| Type of Response-no. (%) | MMR-deficient CRC n = 10 | MRC-proficient CRC n = 18 | MMR-deficient non-CRC n = 7 |
|---|---|---|---|
| Complete Response | 0(0) | 0(0) | 1(14)[1] |
| Partial Response | 4(40) | 0(0) | 4(57)[2] |
| Stable Disease (Week 12) | 5(50) | 2(11) | 0(0) |
| Progressive Disease | 1(10) | 11(61) | 2(29) |
| Not Evaluable[3] | 0(0) | 5(28) | 0(0) |
| Objective Response Rate (%) | 40 | 0 | 71 |
| 95% Cl | 12-74 | 0-19 | 29-96 |
| Disease Control Rate (%)[4] | 90 | 11 | 71 |
| 95% Cl | 55-100 | 1-35 | 29-96 |
| Duration of Response-median weeks | Not reached | N/A[5] | Not reached |
| Time to Response, median weeks (range) | 28 (13-35) | N/A[5] | 11(10-13) |

[1]Originally PR at 12 weeks that was converted to CR at 20 weeks
[2]One PR at 12 weeks
[3]Patients were considered not evaluable if they did not undergo a 12 week scan due to clinical progression.
[4]The rate of disease control was defined as the percentage of patients who had a complete response, partial response or stable disease for 12 weeks or more.
[5]No responses recorded for MMR-proficient CRC patients

TABLE 3

Drug-Related Adverse Events

| Event-no (%)[1] | All Grades N = 41 | Grade 3 or 4 N = 41 |
|---|---|---|
| Any | 40(98) | 17(41) |
| Blood and Lymphatic | | |
| Anemia | 8(20) | 7(17) |
| Lymphopenia | 8(20) | 8(20) |
| Cardiac | | |
| Sinus tachycardia | 4(10) | 0 |
| Dermatologic | | |
| Dry skin | 5(12) | 0 |
| Rash/pruritis | 10(24) | 0 |
| Endocrine Disorders | | |
| Thyroiditis/Hypothyroidism/Hypophysitis | 4(10) | 0 |
| Gastrointestinal | | |
| Abdominal Pain | 10(24) | 0 |
| Anorexia | 4(10) | 0 |
| Constipation | 8(20) | 0 |
| Diarrhea | 10(24) | 2(5) |
| Dry mouth | 5(12) | 0 |
| Nausea | 5(12) | 0 |
| Bowel Obstruction | 3(7) | 3(7) |
| Hepatobiliary | | |
| ALT, elevated | 3(7) | 2(5) |
| Pancreatitis[2] | 6(15) | 0 |
| Metabolism and Nutrition | | |
| Hypoalbuminemia | 4(10) | 4(10) |
| Hyponatremia | 3(7) | 3(7) |
| Musculoskeletal | | |
| Arthralgia | 7(17) | 0 |
| Myalgia | 6(15) | 0 |
| Nervous System | | |
| Dizziness | 4(10) | 0 |
| Headache | 7(17) | 0 |
| Psychiatric | | |
| Insomnia | 3(7) | 0 |
| Respiratory[3] | | |
| Allergic Rhinitis | 12(29) | 0 |
| Cough | 4(10) | 0 |
| Dyspnea | 6(15) | 0 |
| Upper Respiratory Infection | 3(7) | 0 |

TABLE 3-continued

Drug-Related Adverse Events

| Event-no (%)[1] | All Grades N = 41 | Grade 3 or 4 N = 41 |
|---|---|---|
| Other | | |
| Cold intolerance | 6(15) | 0 |
| Edema | 4(10) | 0 |
| Fatigue | 13(32) | 0 |
| Fever | 5(12) | 0 |
| Pain | 14(34) | 0 |

[1]Adverse Events occurring in greater than 5% of patients
[2]All cases of pancreatitis were asymptomatic
[3]One incidence of pneumonitis (2%)

References

The Disclosure of Each Feference Cited is Expressly Incorporated Herein.

1. Nishimura H, Okazaki T, Tanaka Y, et al. Autoimmune Dilated Cardiomyopathy in PD-1 Receptor-Deficient Mice. Science 2001;291:319-22.
2. Chen L. Co-inhibitory molecules of the B7-CD28 family in the control of T-cell immunity. Nat Rev Immunol 2004;4:336-47.
3. Nishimura H, Nose M, Hiai H, Minato N, Honjo T. Development of Lupus-like Autoimmune Diseases by Disruption of the PD-1 Gene Encoding an ITIM Motif-Carrying Immunoreceptor. Immunity 1999;11:141-51.
4. Ansell S M, Lesokhin A M, Borrello I, et al. PD-1 Blockade with Nivolumab in Relapsed or Refractory Hodgkin's Lymphoma. The New England journal of medicine 2015;372:311-9.
5. Hamid 0, Robert C, Daud A, et al. Safety and tumor responses with lambrolizumab (anti-PD-1) in melanoma. The New England journal of medicine 2013;369:134-44.
6. Herbst R S, Soria J C, Kowanetz M, et al. Predictive correlates of response to the anti-PD-L1 antibody MPDL3280A in cancer patients. Nature 2014;515:563-7.
7. Powles T, Eder J P, Fine G D, et al. MPDL3280A (anti-PD-L1) treatment leads to clinical activity in metastatic bladder cancer. Nature 2014;515:558-62.
8. Topalian S L, Sznol M, McDermott D F, et al. Survival, durable tumor remission, and long-term safety in patients with advanced melanoma receiving nivolumab. Journal of clinical oncology : official journal of the American Society of Clinical Oncology 2014;32:1020-30.
9. Brahmer J R, Tykodi S S, Chow L Q, et al. Safety and activity of anti-PD-L1 antibody in patients with advanced cancer. The New England journal of medicine 2012;366: 2455-65.
10. Topalian S L, Hodi F S, Brahmer J R, et al. Safety, activity, and immune correlates of anti-PD-1 antibody in cancer. The New England journal of medicine 2012;366: 2443-54.
11. Taube J M, Klein A, Brahmer J R, et al. Association of PD-1, PD-1 ligands, and other features of the tumor immune microenvironment with response to anti-PD-1 therapy. Clinical cancer research : an official journal of the American Association for Cancer Research 2014;20:5064-74.
12. Brahmer J R, Drake C G, Wollner I, et al. Phase I study of single-agent anti-programmed death-1 (MDX-1106) in refractory solid tumors: safety, clinical activity, pharmacodynamics, and immunologic correlates. Journal of clinical oncology : official journal of the American Society of Clinical Oncology 2010;28:3167-75.
13. Koopman M, Kortman GAM, Mekenkamp L, et al. Deficient mismatch repair system in patients with sporadic advanced colorectal cancer. Br J Cancer 0000;100:266-73.
14. Goldstein J, Tran B, Ensor J, et al. Multicenter retrospective analysis of metastatic colorectal cancer (CRC) with high-level microsatellite instability (MSI-H). Annals of oncology : official journal of the European Society for Medical Oncology/ESMO 2014;25:1032-8.
15. Segal N H, Parsons D W, Peggs KS, et al. Epitope landscape in breast and colorectal cancer. Cancer research 2008;68:889-92.
16. Timmermann B, Kerick M, Roehr C, et al. Somatic mutation profiles of MSI and MSS colorectal cancer identified by whole exome next generation sequencing and bioinformatics analysis. PloS one 2010;5:e15661.
17. Eshleman J R, Lang E Z, Bowerfind G K, et al. Increased mutation rate at the hprt locus accompanies microsatellite instability in colon cancer. Oncogene 1995;10:33-7.
18. Comprehensive molecular characterization of human colon and rectal cancer. Nature 2012;487:330-7.
19. Dolcetti R, Viel A, Doglioni C, et al. High prevalence of activated intraepithelial cytotoxic T lymphocytes and increased neoplastic cell apoptosis in colorectal carcinomas with microsatellite instability. The American journal of pathology 1999;154:1805-13.
20. Alexander J, Watanabe T, Wu TT, Rashid A, Li S, Hamilton S R. Histopathological identification of colon cancer with microsatellite instability. The American journal of pathology 2001;158:527-35.
21. Smyrk T C, Watson P, Kaul K, Lynch H T. Tumor-infiltrating lymphocytes are a marker for microsatellite instability in colorectal carcinoma. Cancer 2001;91:2417-22.
22. Young J, Simms L A, Biden K G, et al. Features of colorectal cancers with high-level microsatellite instability occurring in familial and sporadic settings: parallel pathways of tumorigenesis. The American journal of pathology 2001;159:2107-16.
23. Berger M F, Hodis E, Heffernan T P, et al. Melanoma genome sequencing reveals frequent PREX2 mutations. Nature 2012;485:502-6.
24. Lee W, Jiang Z, Liu J, et al. The mutation spectrum revealed by paired genome sequences from a lung cancer patient. Nature 2010;465:473-7.
25. Lipson E J, Sharfman WH, Drake C G, et al. Durable cancer regression off-treatment and effective reinduction therapy with an anti-PD-1 antibody. Clinical cancer research : an official journal of the American Association for Cancer Research 2013;19:462-8.
26. Boland C R, Goel A. Microsatellite instability in colorectal cancer. Gastroenterology 2010;138:2073-87 e3.
27. Lynch HT, de la Chapelle A. Hereditary colorectal cancer. The New England journal of medicine 2003;348: 919-32.
28. Yamamoto H, Imai K, Perucho M. Gastrointestinal cancer of the microsatellite mutator phenotype pathway. Journal of gastroenterology 2002;37:153-63.
29. Herman J G, Umar A, Polyak K, et al. Incidence and functional consequences of hMLH1 promoter hypermethylation in colorectal carcinoma. Proceedings of the National Academy of Sciences of the United States of America 1998;95:6870-5.
30. Jones S, Anagnostou V, Lytle K, et al. Personalized genomic analyses for cancer mutation discovery and interpretation. Science translational medicine 2015;7:283ra53.

31. Lundegaard C, Lamberth K, Harndahl M, Buus S, Lund O, Nielsen M. NetMHC-3.0: accurate web accessible predictions of human, mouse and monkey MEW class I affinities for peptides of length 8-11. Nucleic acids research 2008;36:W509-12.

32. Lundegaard C, Lund O, Nielsen M. Accurate approximation method for prediction of class I MEW affinities for peptides of length 8, 10 and 11 using prediction tools trained on 9mers. Bioinformatics 2008;24:1397-8.

33. Wolchok J D, Hoos A, O'Day S, et al. Guidelines for the evaluation of immune therapy activity in solid tumors: immune-related response criteria. Clinical cancer research : an official journal of the American Association for Cancer Research 2009;15:7412-20.

34. Maple J T, Smyrk T C, Boardman L A, Johnson R A, Thibodeau S N, Chari S T. Defective DNA mismatch repair in long-term (>or =3 years) survivors with pancreatic cancer. Pancreatology 2005;5:220-7; discussion 7-8.

35. Meltzer S J, Yin J, Manin B, et al. Microsatellite instability occurs frequently and in both diploid and aneuploid cell populations of Barrett's-associated esophageal adenocarcinomas. Cancer research 1994;54:3379-82.

36. Nakata B, Wang Y Q, Yashiro M, et al. Prognostic value of microsatellite instability in resectable pancreatic cancer. Clinical cancer research: an official journal of the American Association for Cancer Research 2002;8:2536-40.

37. Comprehensive molecular characterization of gastric adenocarcinoma. Nature 2014;513:202-9.

38. Agaram N P, Shia J, Tang L H, Klimstra D S. DNA mismatch repair deficiency in ampullary carcinoma: a morphologic and immunohistochemical study of 54 cases. American journal of clinical pathology 2010;133:772-80.

39. Kandoth C, Schultz N, Cherniack A D, et al. Integrated genomic characterization of endometrial carcinoma. Nature 2013;497:67-73.

40. Garg K, Leitao MINI, Jr., Kauff N D, et al. Selection of endometrial carcinomas for DNA mismatch repair protein immunohistochemistry using patient age and tumor morphology enhances detection of mismatch repair abnormalities. The American journal of surgical pathology 2009;33: 925-33.

41. Snyder A, Makarov V, Merghoub T, et al. Genetic basis for clinical response to CTLA-4 blockade in melanoma. The New England journal of medicine 2014;371: 2189-99.

42. Williams AS, Huang W Y. The analysis of microsatellite instability in extracolonic gastrointestinal malignancy. Pathology 2013;45:540-52.

43. Jones S, Emmerson P, Maynard J, et al. Biallelic germline mutations in MYH predispose to multiple colorectal adenoma and somatic G:C→T:A mutations. Human Molecular Genetics 2002;11:2961-7.

44. Palles C, Cazier J-B, Howarth K M, et al. Germline mutations affecting the proofreading domains of POLE and POLD1 predispose to colorectal adenomas and carcinomas. Nature genetics 2013;45:136-44.

45. Bodmer W, Bishop T, Karran P. Genetic steps in colorectal cancer. Nature genetics 1994;6:217-9.

46. Kim H, Jen J, Vogelstein B, Hamilton S R. Clinical and pathological characteristics of sporadic colorectal carcinomas with DNA replication errors in microsatellite sequences. The American journal of pathology 1994;145: 148-56.

47. Llosa NJ, Cruise M, Tam A, et al. The vigorous immune microenvironment of microsatellite instable colon cancer is balanced by multiple counter-inhibitory checkpoints. Cancer Discov 2015:43-51. [This disclosure was made by some of the joint inventors.]

48. Rizvi N A, Hellmann M D, Snyder A, et al. Mutational landscape determines sensitivity to PD-1 blockade in non-small cell lung cancer. Science 2015.

49. Gubin M M, Zhang X, Schuster H, et al. Checkpoint blockade cancer immunotherapy targets tumour-specific mutant antigens. Nature 2014;515:577-81.

50. Linnemann C, van Buuren M M, Bies L, et al. High-throughput epitope discovery reveals frequent recognition of neo-antigens by CD4+ T cells in human melanoma. Nature medicine 2015;21:81-5.

51. Lipson E J, Velculescu V E, Pritchard T S, et al. Circulating tumor DNA analysis as a real-time method for monitoring tumor burden in melanoma patients undergoing treatment with immune checkpoint blockade. Journal for immunotherapy of cancer 2014;2:42.

52. Diaz L A, Jr., Bardelli A. Liquid biopsies: genotyping circulating tumor DNA. Journal of clinical oncology : official journal of the American Society of Clinical Oncology 2014;32:579-86.

53. Yadav M, Jhunjhunwala S, Phung Q T, et al. Predicting immunogenic tumour mutations by combining mass spectrometry and exome sequencing. Nature 2014;515:572-6.

We claim:

1. A method for treating cancer in a patient in need thereof,
wherein a tumor sample obtained from the patient has been determined to exhibit an instability of one or more microsatellite markers or a deficiency of one or more mismatch repair markers, the patient having received a prior cancer therapy drug to treat the tumor, the method comprising:
administering an effective amount of pembrolizumab to the patient;
wherein the patient exhibits an outcome that is improved as compared to a corresponding outcome that would be observed in a reference patient that has been administered pembrolizumab, wherein the reference patient has a tumor that does not exhibit an instability of the one or more microsatellite markers or a deficiency of the one or more mismatch repair markers.

2. The method of claim 1, wherein the cancer in the patient has progressed after the patient received the prior cancer therapy drug.

3. The method of claim 1, wherein the outcome that is improved is an improved objective response rate (ORR), an improved progression-free survival (PFS), or an improved overall survival (OS).

4. The method of claim 1, wherein the tumor sample from the patient exhibits an instability of one or more microsatellite markers, wherein the microsatellite marker is BAT-25, BAT-26, MONO-27, NR-21 or NR-24, or
wherein the tumor sample from the patient exhibits a deficiency of one or more mismatch repair markers, wherein the mismatch repair marker is POLE, POLD1, or MYH.

5. The method of claim 1, wherein the cancer is a metastatic cancer.

6. The method of claim 1, wherein the cancer is a metastatic colorectal cancer.

7. The method of claim 1, wherein pembrolizumab is administered by intravenous infusion.

* * * * *